(12) United States Patent
Inoue et al.

(10) Patent No.: US 9,917,261 B2
(45) Date of Patent: Mar. 13, 2018

(54) ORGANIC COMPOUND, LIGHT-EMITTING ELEMENT, DISPLAY MODULE, LIGHTING MODULE, LIGHT-EMITTING DEVICE, DISPLAY DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Yui Yamada, Kanagawa (JP); Tsunenori Suzuki, Kanagawa (JP); Satoshi Seo, Kanagawa (JP)

(73) Assignee: Semiconductor Energy Laboratory Co., Ltd. (JP)

(*) Notice: Subject to any disclaimer, the term of this patent is extended or adjusted under 35 U.S.C. 154(b) by 538 days.

(21) Appl. No.: 14/537,230

(22) Filed: Nov. 10, 2014

(65) Prior Publication Data
US 2015/0131302 A1 May 14, 2015

(30) Foreign Application Priority Data
Nov. 13, 2013 (JP) .................. 2013-234790

(51) Int. Cl.
| | | |
|---|---|---|
| H01L 51/00 | (2006.01) | |
| F21V 23/04 | (2006.01) | |
| C09K 11/06 | (2006.01) | |
| C07D 405/14 | (2006.01) | |
| H01L 51/50 | (2006.01) | |

(52) U.S. Cl.
CPC ........ *H01L 51/0072* (2013.01); *C07D 405/14* (2013.01); *C09K 11/06* (2013.01); *H01L 51/0067* (2013.01); *H01L 51/0073* (2013.01); *H01L 51/5072* (2013.01)

(58) Field of Classification Search
None
See application file for complete search history.

(56) References Cited

U.S. PATENT DOCUMENTS

| | | | |
|---|---|---|---|
| 8,354,542 B2 | 1/2013 | Kawata et al. | |
| 2007/0037983 A1 | 2/2007 | Nomura et al. | |
| 2009/0284138 A1* | 11/2009 | Yasukawa ............ | C09K 11/06 313/504 |

(Continued)

FOREIGN PATENT DOCUMENTS

| | | | |
|---|---|---|---|
| JP | 2009-184987 | | 8/2009 |
| JP | 2012-018958 A | * | 1/2012 |

(Continued)

OTHER PUBLICATIONS

"Phenanthryl." Merriam-Webster.com. Merriam-Webster, n.d. Web. Feb. 27, 2017.*

(Continued)

*Primary Examiner* — Dawn L Garrett
(74) *Attorney, Agent, or Firm* — Husch Blackwell LLP

(57) ABSTRACT

A novel organic compound is provided. Alternatively, an organic compound that can be used as an electron-transport material of a light-emitting element is provided. An organic compound in which heteroaromatic groups each including two pyridine rings are bonded to the 2- and 8-positions of dibenzofuran is provided. The organic compound is an organic compound that can be used as an electron-transport material of a light-emitting element.

16 Claims, 19 Drawing Sheets

(56) References Cited

U.S. PATENT DOCUMENTS

| | | | |
|---|---|---|---|
| 2011/0006670 A1* | 1/2011 | Katakura | C07D 403/10 |
| | | | 313/504 |
| 2011/0210316 A1 | 9/2011 | Kadoma et al. | |
| 2012/0098417 A1 | 4/2012 | Inoue et al. | |
| 2012/0157694 A1 | 6/2012 | Osaka et al. | |
| 2012/0184755 A1 | 7/2012 | Osaka et al. | |
| 2012/0193613 A1 | 8/2012 | Kadoma et al. | |
| 2013/0214260 A1 | 8/2013 | Kadoma et al. | |
| 2014/0077191 A1* | 3/2014 | Mizutani | C07D 471/04 |
| | | | 257/40 |
| 2015/0104636 A1* | 4/2015 | Takemura | H01B 1/02 |
| | | | 428/336 |

FOREIGN PATENT DOCUMENTS

| | | | |
|---|---|---|---|
| JP | 2013/242988 A | * | 12/2013 |
| JP | 2014-044972 A | * | 3/2014 |
| WO | WO 2014/042163 A1 | * | 3/2014 |

OTHER PUBLICATIONS

European Journal of Inorganic Chemistry, (2010), (20), pp. 3135-3142.*

* cited by examiner

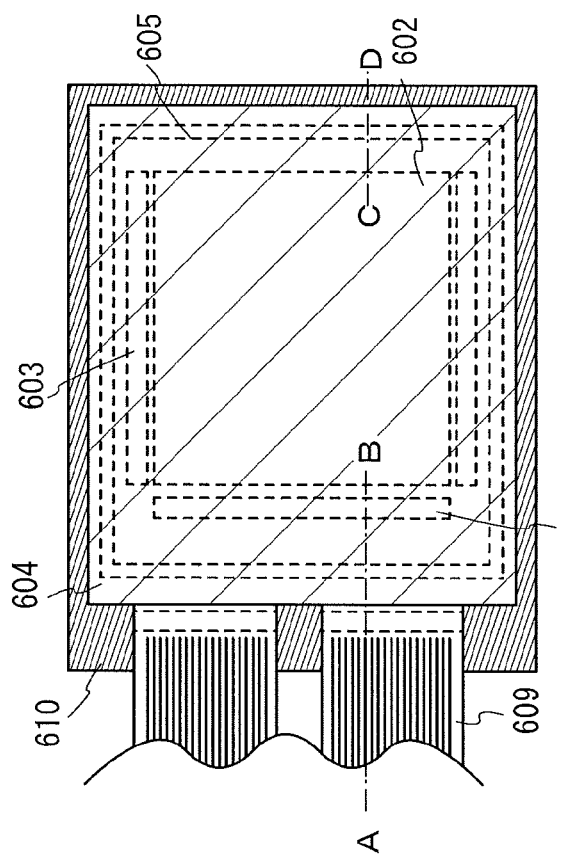
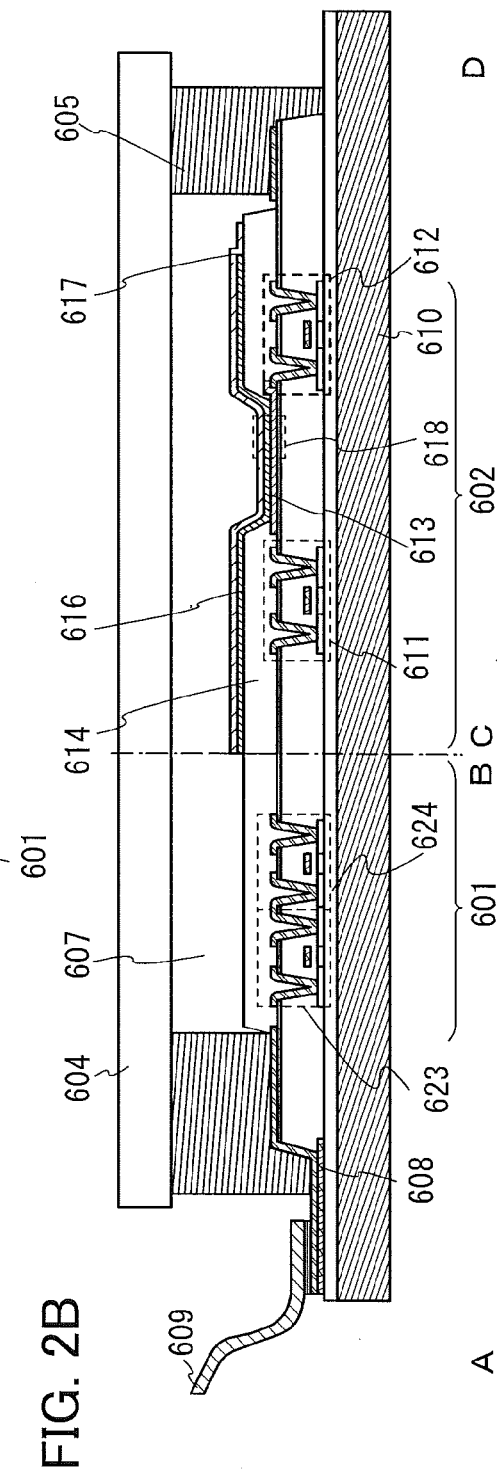
FIG. 2A
FIG. 2B

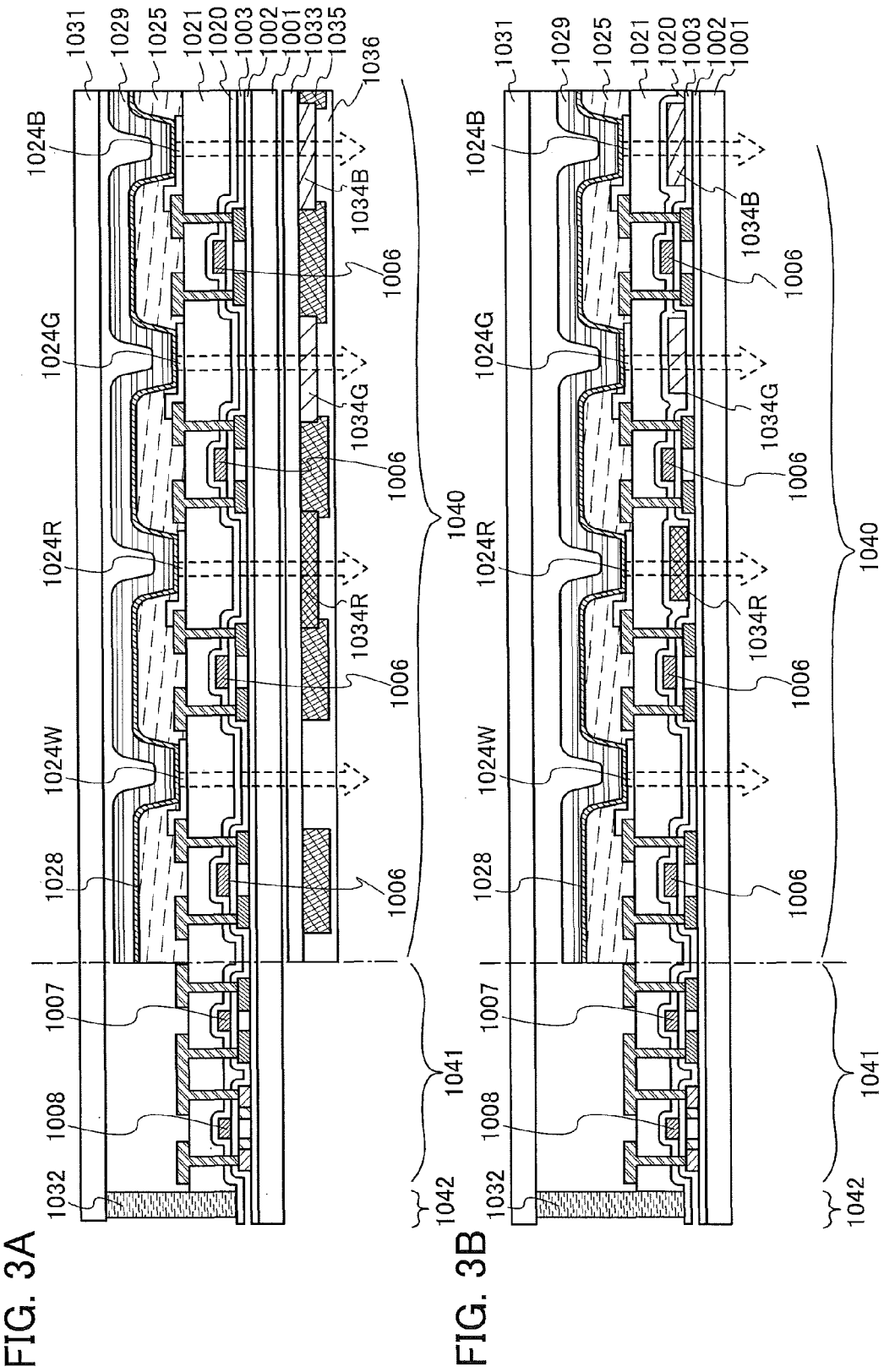

FIG. 7A
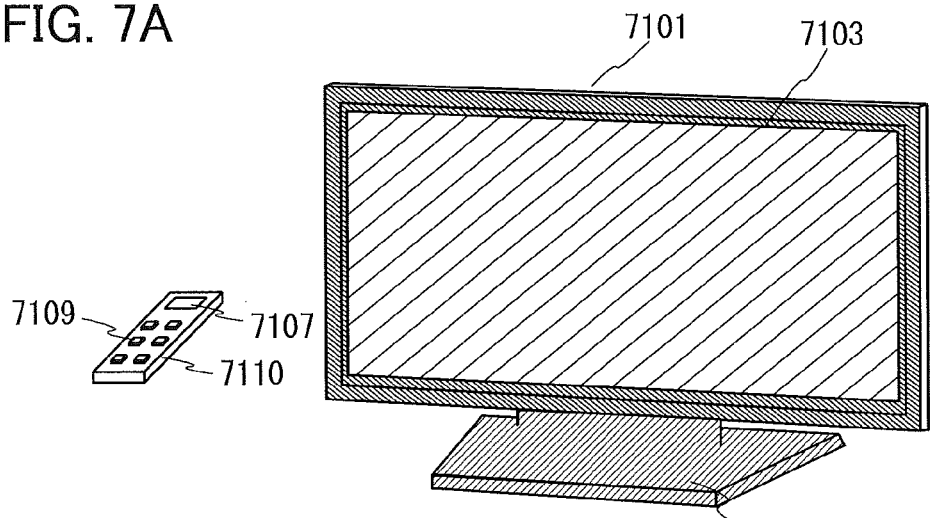
FIG. 7B1
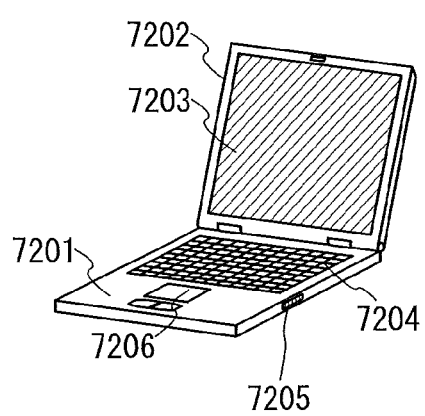
FIG. 7B2
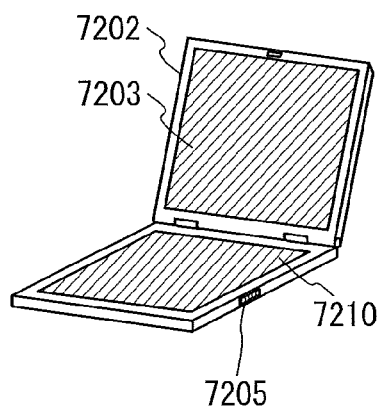
FIG. 7C
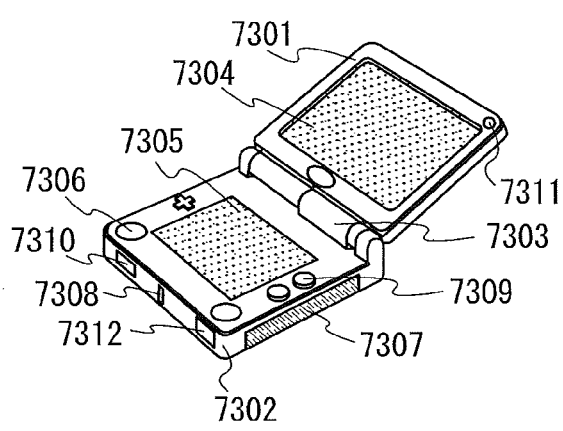
FIG. 7D
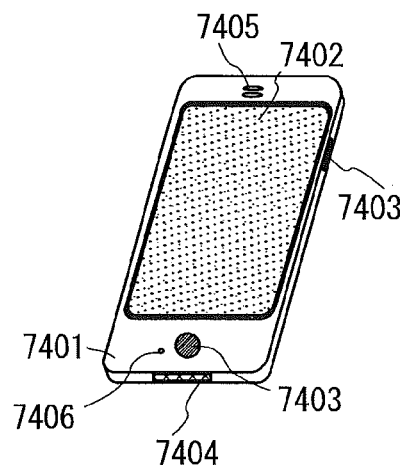

ORGANIC COMPOUND, LIGHT-EMITTING ELEMENT, DISPLAY MODULE, LIGHTING MODULE, LIGHT-EMITTING DEVICE, DISPLAY DEVICE, ELECTRONIC DEVICE, AND LIGHTING DEVICE

BACKGROUND OF THE INVENTION

1. Field of the Invention

One embodiment of the present invention relates to an organic compound, and a light-emitting element, a display module, a lighting module, a display device, a light-emitting device, an electronic device, and a lighting device each including the organic compound.

Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a light-emitting device, a power storage device, a storage device, a method for driving any of them, and a method for manufacturing any of them.

2. Description of the Related Art

Light-emitting elements (organic EL elements) including organic compounds and utilizing electroluminescence (EL) have been put to more practical use. In the basic structure of such light-emitting elements, an organic compound layer containing a light-emitting substance (an EL layer) is interposed between a pair of electrodes. By voltage application to an element, light emission from the light-emitting substance can be obtained.

Since such light-emitting elements are of self-light-emitting type, light-emitting elements have advantages over liquid crystal displays when used as pixels of a display in that visibility of pixels is high and backlight is not required. Thus, light-emitting elements are suitable as flat panel display elements. In addition, it is also a great advantage that a display including such light-emitting elements can be manufactured as a thin and lightweight display. Furthermore, extremely high response speed is also a feature thereof.

Since light-emitting layers of such a light-emitting element can be successively formed two-dimensionally, planar light emission can be achieved. This feature is difficult to realize with point light sources typified by incandescent lamps and LEDs or linear light sources typified by fluorescent lamps. Thus, light-emitting elements also have great potential as planar light sources applied to lighting devices and the like.

Despite their suitability for a variety of electronic devices, displays or lighting devices including light-emitting elements as described above have plenty of room to improve their performance and cost competitiveness. In order to achieve this, materials that have better characteristics and are easier to handle are required.

Patent Document

[Patent Document 1] Japanese Published Patent Application No. 2009-184987

SUMMARY OF THE INVENTION

In view of the above, an object of one embodiment of the present invention is to provide a novel organic compound. An object of another embodiment of the present invention is to provide an organic compound that can be used as an electron-transport material of a light-emitting element.

Furthermore, an object of another embodiment of the present invention is to provide a novel light-emitting element. Another object is to provide a light-emitting element, a display module, a lighting module, a light-emitting device, a display device, an electronic device, and a lighting device each having low drive voltage.

It is only necessary that at least one of the above-described objects be achieved in the present invention. Other objects will be apparent from and can be derived from the description of the specification, the drawings, the claims, and the like.

One embodiment of the present invention provides an organic compound in which heteroaromatic groups each including two pyridine rings are bonded to the 2- and 8-positions of dibenzofuran. The organic compound is an organic compound that can be used as an electron-transport material of a light-emitting element.

The organic compound can be represented by the following general formula (G1).

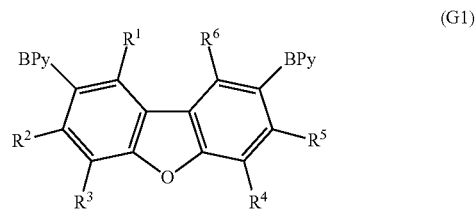

In the general formula (G1), BPy represents a heteroaromatic group including two pyridine rings, and $R^1$ to $R^6$ separately represent an alkyl group having 1 to 6 carbon atoms or a substituted or unsubstituted phenyl group.

An organic compound of another embodiment of the present invention can also be represented by the following general formula (G2).

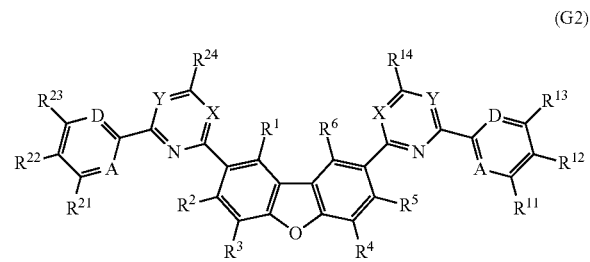

In the general formula (G2), $R^1$ to $R^6$, $R^{11}$ to $R^{14}$, and $R^{21}$ to $R^{24}$ separately represent an alkyl group having 1 to 6 carbon atoms or a substituted or unsubstituted phenyl group. In addition, X and Y separately represent a carbon atom or a nitrogen atom. Furthermore, A and D separately represent a carbon atom or a nitrogen atom, and at least one of A and D represents a nitrogen atom. When any of A, D, X, and Y represents a carbon atom having one or more substituents, the substituents may be bonded to each other to form a ring.

The above organic compound preferably includes a pyrimidine skeleton, and such an organic compound can be represented by the following general formula (G3).

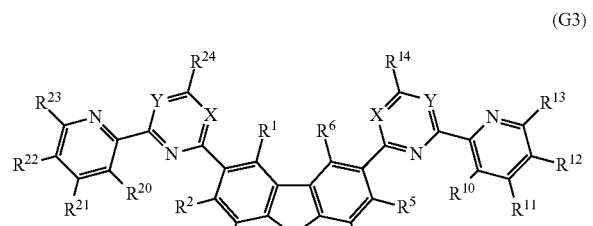

(G3)

In the general formula (G3), $R^1$ to $R^6$, $R^{10}$ to $R^{14}$, and $R^{20}$ to $R^{24}$ separately represent an alkyl group having 1 to 6 carbon atoms or a substituted or unsubstituted phenyl group. In addition, one of X and Y represents a carbon atom and the other of X and Y represents a nitrogen atom.

Another structure of one embodiment of the present invention is an organic compound represented by the following general formula (G4).

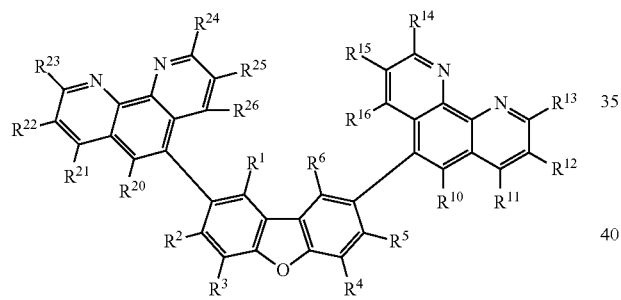

(G4)

In the general formula (G4), $R^1$ to $R^6$, $R^{10}$ to $R^{16}$, and $R^{20}$ to $R^{26}$ separately represent an alkyl group having 1 to 6 carbon atoms or a substituted or unsubstituted phenyl group.

Another structure of one embodiment of the present invention is an organic compound represented by the following general formula (G5).

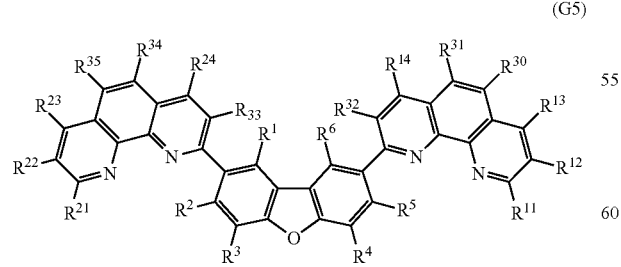

(G5)

In the general formula (G5), $R^1$ to $R^6$, $R^{11}$ to $R^{14}$, $R^{21}$ to $R^{24}$, and $R^{30}$ to $R^{35}$ separately represent an alkyl group having 1 to 6 carbon atoms or a substituted or unsubstituted phenyl group.

Another embodiment of the present invention is an organic compound represented by the following structural formula (100).

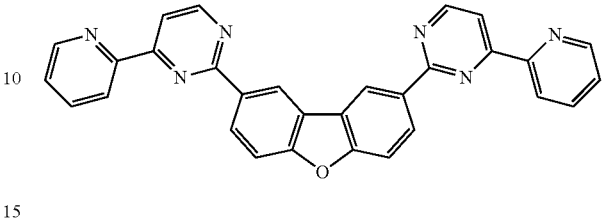

(100)

Another embodiment of the present invention is an organic compound represented by the following structural formula (200).

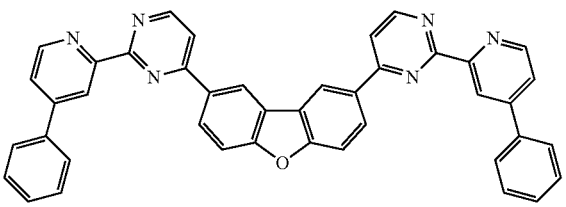

(200)

Another embodiment of the present invention is an organic compound represented by the following structural formula (300).

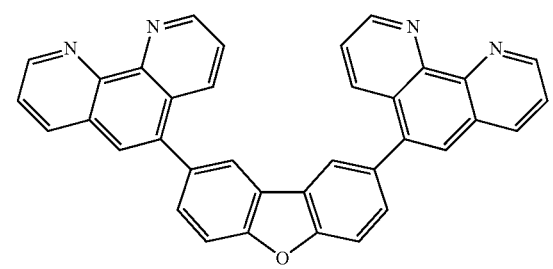

(300)

Another embodiment of the present invention is an organic compound represented by the following structural formula (400).

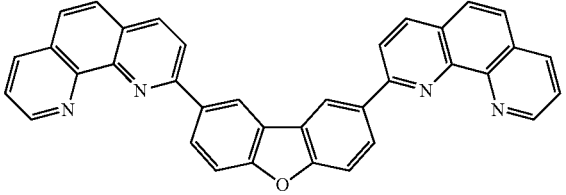

(400)

Another embodiment of the present invention is a light-emitting element including the above organic compound.

Another embodiment of the present invention is a light-emitting element including the above organic compound in an electron-transport layer.

Another embodiment of the present invention is a display module including the above light-emitting element.

Another embodiment of the present invention is a lighting module including the above light-emitting element.

Another embodiment of the present invention is a light-emitting device including the above light-emitting element and a unit capable of controlling the light-emitting element.

Another embodiment of the present invention is a display device that includes the above-described light-emitting element in a display portion and a unit capable of controlling the light-emitting element.

Another embodiment of the present invention is a lighting device that includes the above-described light-emitting element in a lighting portion and a unit capable of controlling the light-emitting element.

Another embodiment of the present invention is an electronic device that includes the above-described light-emitting element.

Note that the light-emitting device in this specification includes an image display device including a light-emitting element. Furthermore, the light-emitting device may be included in a module in which a light-emitting element is provided with a connector such as an anisotropic conductive film or a tape carrier package (TCP), a module in which a printed wiring board is provided at the end of a TCP, and a module in which an integrated circuit (IC) is directly mounted on a light-emitting element by a chip on glass (COG) method. The light-emitting device may be included in lighting equipment or the like.

According to one embodiment of the present invention, a novel organic compound can be provided. According to another embodiment of the present invention, an organic compound that can be used as an electron-transport material of a light-emitting element can be provided.

According to another embodiment of the present invention, a light-emitting element, a display module, a lighting module, a light-emitting device, a display device, an electronic device, and a lighting device each having low drive voltage can be provided.

It is only necessary that at least one of the above effects be achieved in the present invention. Other effects will be apparent from and can be derived from the description of the specification, the drawings, the claims, and the like.

BRIEF DESCRIPTION OF THE DRAWINGS

In the accompanying drawings:

FIGS. 2A and 2B are conceptual views of an active matrix light-emitting device;

FIGS. 3A and 3B are conceptual views of active matrix light-emitting devices;

FIGS. 7A, 7B1, 7B2, 7C, and 7D illustrate electronic devices;

DETAILED DESCRIPTION OF THE INVENTION

Figure 1A:
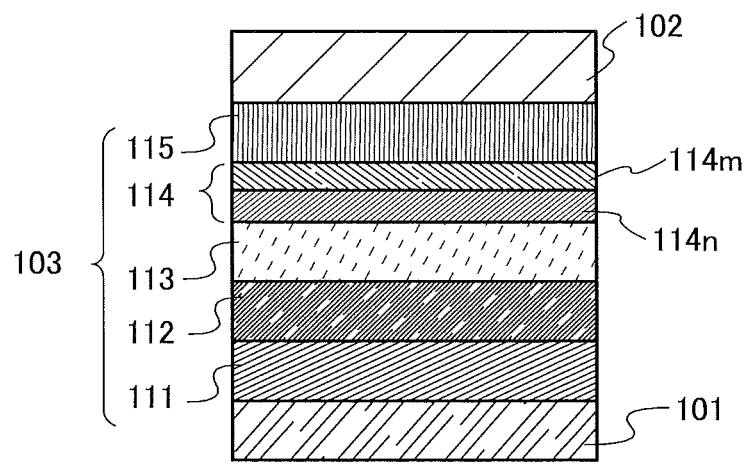
FIGS. 1A and 1B are conceptual views of light-emitting elements.

An embodiment of the present invention is described below with reference to the drawings. Note that the present invention is not limited to the following description, and it is easily understood by those skilled in the art that various changes and modifications can be made without departing from the spirit and scope of the present invention. Therefore, the present invention should not be construed as being limited to the description in the following embodiment.

The present inventors have found that an organic compound in which heteroaromatic groups each including two pyridine rings are bonded to the 2- and 8-positions of dibenzofuran has a high electron-transport property and can be suitably used as a material of a light-emitting element.

Because of the above-described high electron-transport property, the organic compound in which heteroaromatic groups each including two pyridine rings are bonded to the 2- and 8-positions of dibenzofuran is preferably used as a material of an electron-transport layer in a light-emitting element.

Such an organic compound in which heteroaromatic groups each including two pyridine rings are bonded to the 2- and 8-positions of dibenzofuran can be represented by the following general formula (G1).

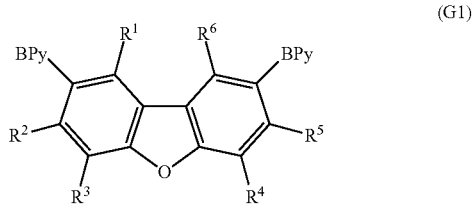

(G1)

In the general formula (G1), BPy represents a substituted or unsubstituted heteroaromatic group including two pyridine rings, and $R^1$ to $R^6$ separately represent an alkyl group having 1 to 6 carbon atoms or a substituted or unsubstituted phenyl group.

Note that when the above heteroaromatic group has a substituent, the substituent can be, for example, an alkyl group having 1 to 6 carbon atoms or a substituted or unsubstituted phenyl group.

An organic compound of another embodiment of the present invention can also be represented by the following general formula (G2).

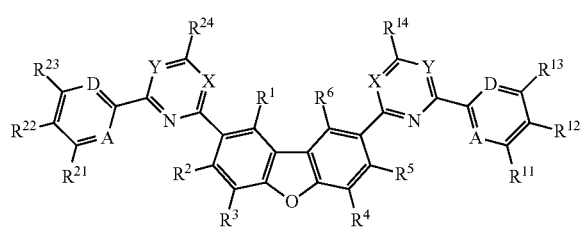

(G2)

In the general formula (G2), $R^1$ to $R^6$, $R^{11}$ to $R^{14}$, and $R^{21}$ to $R^{24}$ separately represent an alkyl group having 1 to 6 carbon atoms or a substituted or unsubstituted phenyl group. In addition, X and Y separately represent a carbon atom or a nitrogen atom. Furthermore, A and D separately represent a carbon atom or a nitrogen atom, and at least one of A and D represents a nitrogen atom. When any of A, D, X, and Y represents a carbon atom, one or more substituents may be included and the substituents may be bonded to each other to form a ring. Each of the substituents can be, for example, an alkyl group having 1 to 6 carbon atoms or a substituted or unsubstituted phenyl group.

The above organic compound preferably includes a pyrimidine skeleton, and such an organic compound can be represented by the following general formula (G3).

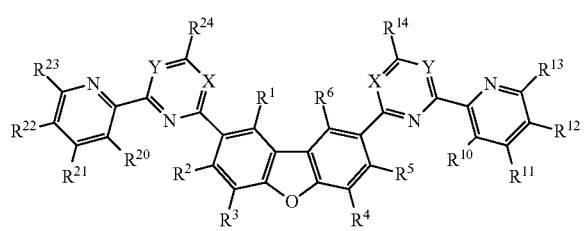

(G3)

In the general formula (G3), $R^1$ to $R^6$, $R^{10}$ to $R^{14}$, and $R^{20}$ to $R^{24}$ separately represent an alkyl group having 1 to 6 carbon atoms or a substituted or unsubstituted phenyl group. In addition, one of X and Y represents a carbon atom and the other of X and Y represents a nitrogen atom.

Furthermore, in the organic compound represented by the above general formula (G1), heteroaromatic groups each including two pyridine rings bonded to the 2- and 8-positions of dibenzofuran may be a phenanthryl group. In other words, another structures of one embodiment of the present invention are organic compounds represented by the following general formulae (G4) and (G5).

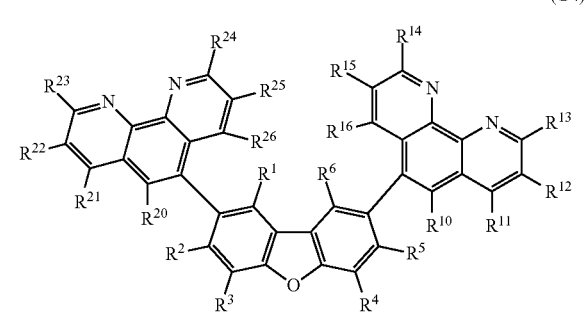

(G4)

In the general formula (G4), $R^1$ to $R^6$, $R^{10}$ to $R^{16}$, and $R^{20}$ to $R^{26}$ separately represent an alkyl group having 1 to 6 carbon atoms or a substituted or unsubstituted phenyl group.

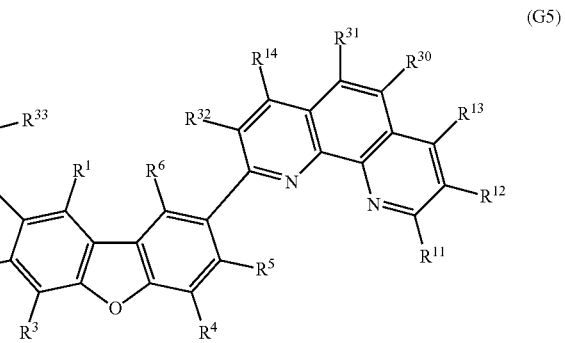

(G5)

In the general formula (G5), $R^1$ to $R^6$, $R^{11}$ to $R^{14}$, $R^{21}$ to $R^{24}$, and $R^{30}$ to $R^{35}$ separately represent an alkyl group having 1 to 6 carbon atoms or a substituted or unsubstituted phenyl group.

Specific examples of the alkyl group having 1 to 6 carbon atoms in the organic compound of one embodiment of the present invention, which is represented by any of the above general formulae (G1) to (G5), include a methyl group, an ethyl group, an n-propyl group, an iso-propyl group, an n-butyl group, an iso-butyl group, a sec-butyl group, a tert-butyl group, a pentyl group, a hexyl group, a cyclohexyl group, and the like.

Specific examples of the organic compound having the above-described structure include the following organic compounds.

(100)
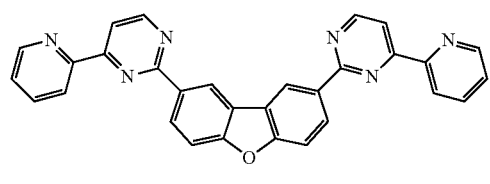
(101)
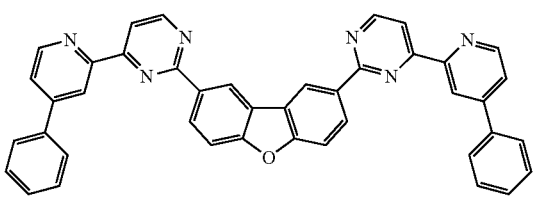
(102)
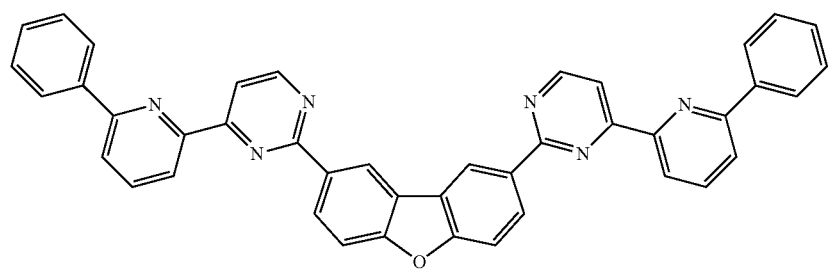
(103)
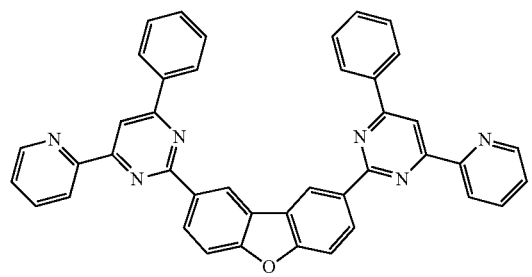
(104)
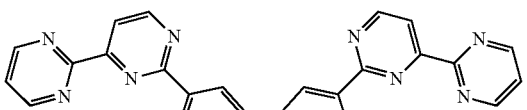
(105)
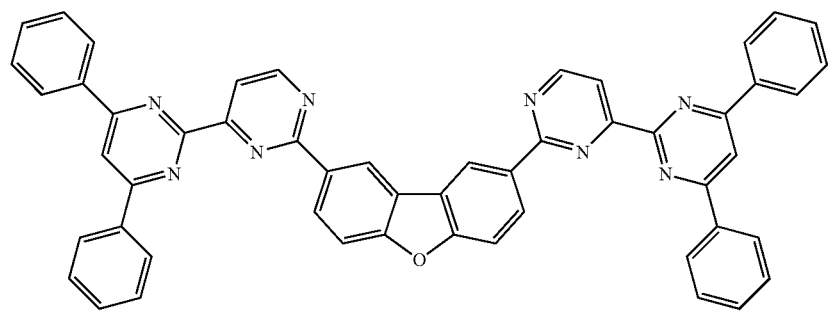
(106)
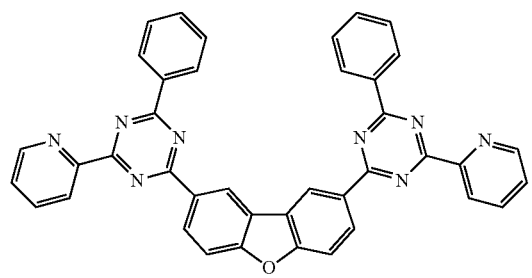
(107)
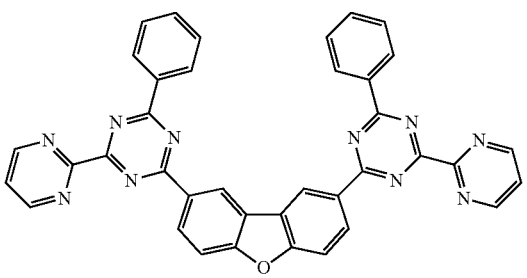
(200)
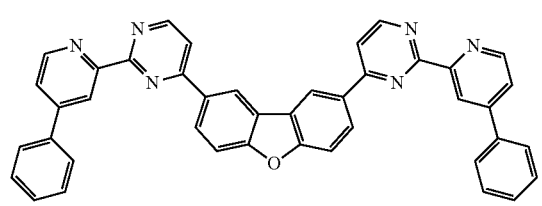
(201)
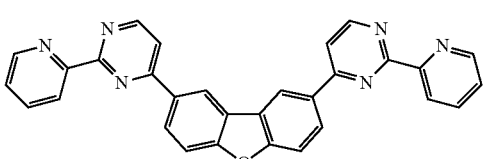

(202)

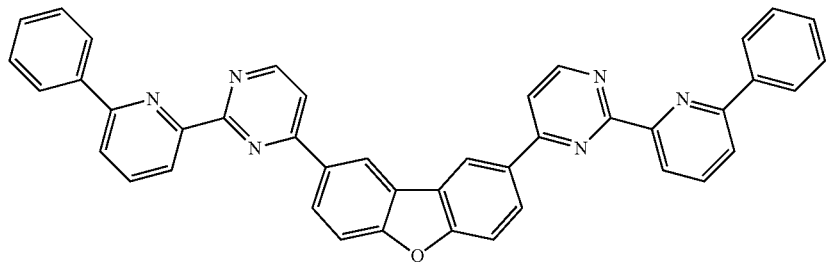

(203)

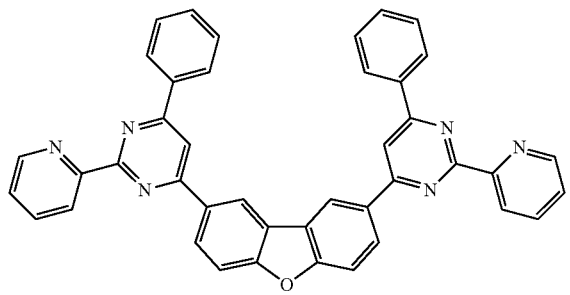

(300)

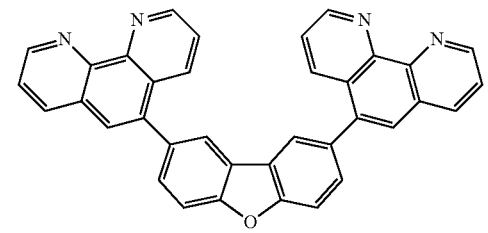

(301)

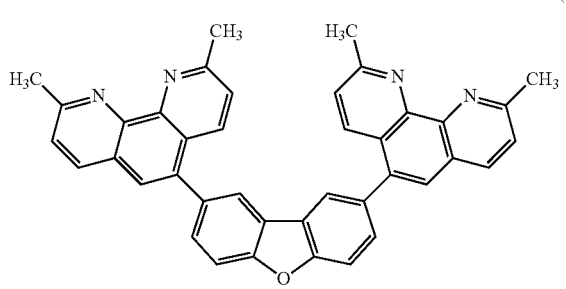

(302)

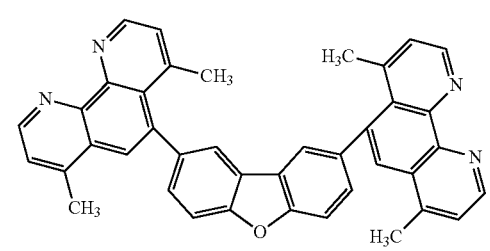

(400)

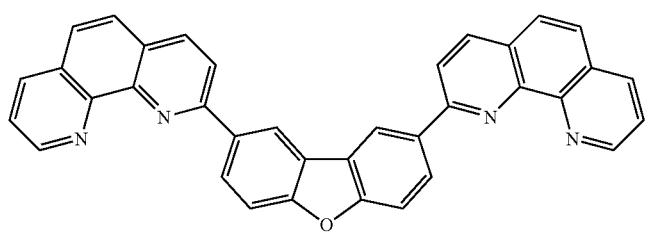

(401)

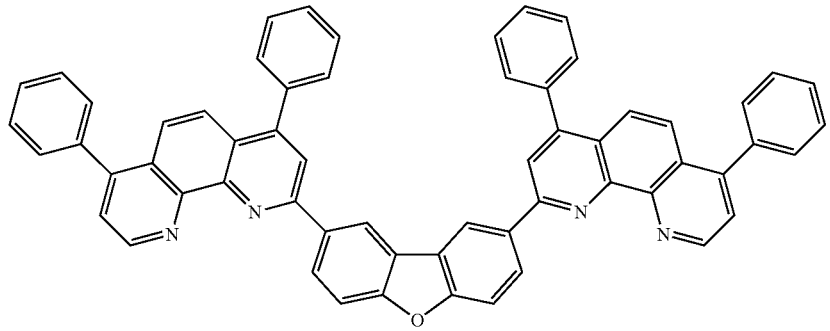

A variety of reactions can be employed as a method of synthesizing the organic compound of one embodiment of the present invention described above. For example, as shown in the following scheme (a), the organic compound can be obtained by making a boronic acid compound (A1) of dibenzofuran or a derivative thereof react with a halogen compound (A2) of a heteroaromatic derivative including two pyridine rings. Note that in the formula, X represents a halogen element. In addition, $B^1$ and $B^2$ represent a boronic acid, a boronic ester, a cyclic-triolborate salt, or the like. As the cyclic-triolborate salt, a lithium salt, a potassium salt, or a sodium salt may be used.

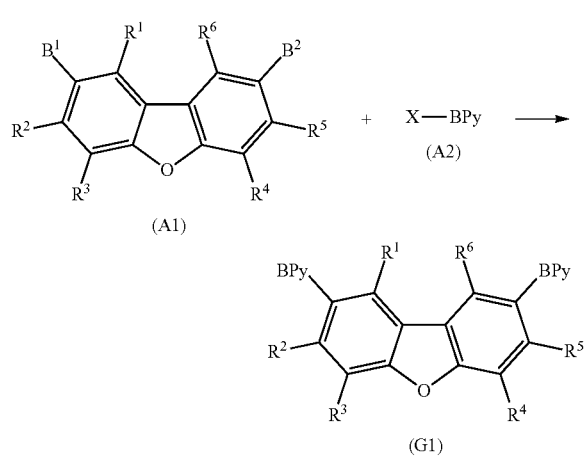

In the synthesis scheme (a), BPy represents a heteroaromatic group including two pyridine rings, and $R^1$ to $R^6$ separately represent an alkyl group having 1 to 6 carbon atoms or a substituted or unsubstituted phenyl group.

Note that a boronic acid compound of the heteroaromatic derivative including two pyridine rings may be reacted with a halogen compound of dibenzofuran or a derivative thereof.

Since a wide variety of compounds (A1) and (A2) are commercially available or their synthesis is feasible, a great variety of the organic compounds represented by the general formula (G1) can be synthesized. Thus, a feature of the organic EL material of one embodiment of the present invention is the abundance of variations. The same applies to the synthesis of the organic compounds represented by the general formulae (G2) to (G5).

Although the example of a method of synthesizing the organic compound of one embodiment of the present invention is described above, one embodiment of the present invention is not limited thereto and any other synthesis method may be employed.

(Light-Emitting Element)

Next, an example of a light-emitting element which is one embodiment of the present invention is described below with reference to FIG. 1A.

In this embodiment, the light-emitting element includes a first electrode 101, a second electrode 102, and an EL layer 103 provided between the first electrode 101 and the second electrode 102. Note that the first electrode 101 functions as an anode and that the second electrode 102 functions as a cathode.

Since the first electrode 101 functions as an anode, it is preferably formed using any of metals, alloys, electrically conductive compounds having a high work function (specifically, a work function of 4.0 eV or more), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Films of such electrically conductive metal oxides are usually formed by a sputtering method, but may be formed by application of a sol-gel method or the like. In an example of the formation method, indium oxide-zinc oxide is deposited by a sputtering method using a target obtained by adding 1 wt % to 20 wt % of zinc oxide to indium oxide. Further, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Another examples are gold (Au), platinum (Pt), nickel (Ni), tungsten (W), chromium (Cr), molybdenum (Mo), iron (Fe), cobalt (Co), copper (Cu), palladium (Pd), nitrides of metal materials (e.g., titanium nitride), and the like. Graphene can also be used. Note that when a composite material described later is used for a layer which is in contact with the first electrode 101 in the EL layer 103, an electrode material can be selected regardless of its work function.

In the EL layer 103, any of the stacked layers preferably includes an organic compound in which heteroaromatic groups each including two pyridine rings are bonded to the 2- and 8-positions of dibenzofuran. The stacked layer structure can be formed by combining a hole-injection layer, a hole-transport layer, a light-emitting layer, an electron-transport layer, an electron-injection layer, a carrier-blocking layer, an intermediate layer, and the like as appropriate. In this embodiment, the EL layer 103 has a structure in which a hole-injection layer 111, a hole-transport layer 112, a light-emitting layer 113, an electron-transport layer 114, and an electron-injection layer 115 are stacked in this order over the first electrode 101. Specific examples of the materials forming the layers are given below.

The hole-injection layer 111 is a layer that contains a substance having a high hole-injection property. Molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: H$_2$Pc) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), a high molecular compound such as poly(3,4-ethylenedioxythiophene)/poly(styrenesulfonic acid) (PEDOT/PSS), or the like.

Alternatively, a composite material in which a substance having a hole-transport property contains a substance having an acceptor property can be used for the hole-injection layer 111. Note that the use of such a substance having a hole-transport property which contains a substance having an acceptor property enables selection of a material used to form an electrode regardless of its work function. In other words, besides a material having a high work function, a material having a low work function can be used for the first electrode 101. As the substance having an acceptor property, 7,7,8,8-tetracyano-2,3,5,6-tetrafluoroquinodimethane (abbreviated to F$_4$-TCNQ), chloranil, and the like can be given. Moreover, oxides of metals belonging to Groups 4 to 8 of the periodic table can be given. Specifically, it is preferable to use vanadium oxide, niobium oxide, tantalum oxide, chromium oxide, molybdenum oxide, tungsten oxide, manganese oxide, and rhenium oxide because of their high electron accepting properties. In particular, molybdenum oxide is more preferable because of its stability in the atmosphere, low hygroscopic property, and easiness of handling.

As the substance having a hole-transport property which is used for the composite material, any of a variety of organic compounds such as aromatic amine compounds, carbazole derivatives, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $10^{-6}$ cm$^2$/Vs or more is preferably used. Organic compounds that can be used as the substance having a hole-transport property in the composite material are specifically given below.

Examples of the aromatic amine compounds are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole derivatives that can be used for the composite material are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of the carbazole derivatives that can be used for the composite material are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbons that can be used for the composite material are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. The aromatic hydrocarbon which has a hole mobility of 1×$10^{-6}$ cm$^2$/Vs or more and which has 14 to 42 carbon atoms is particularly preferable.

Note that the aromatic hydrocarbons that can be used for the composite material may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: poly-TPD) can also be used.

By providing the hole-injection layer 111, a high hole-injection property can be achieved to allow a light-emitting element to be driven at a low voltage.

The hole-transport layer 112 is a layer that contains a substance having a hole-transport property. Examples of the substance having a hole-transport property are aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), and the like. The substances mentioned here have high hole-transport properties and are mainly ones that have a hole mobility of $10^{-6}$ cm$^2$/Vs or more. An organic compound given as an example of the substance having a hole-transport property in the composite material described above can also be used for the hole-transport layer 112. A high molecular compound such as poly(N-vinylcarbazole) (abbreviation: PVK) or poly(4-vinyltriphenylamine) (abbreviation: PVTPA) can also be used. Note that the layer that contains a substance having a hole-transport property is not limited to a single layer, and may be a stack of two or more layers including any of the above substances.

The light-emitting layer 113 may be a layer that emits fluorescence, a layer that emits phosphorescence, or a layer that contains a substance emitting thermally activated delayed fluorescence (TADF) and emits TADF. Furthermore, the light-emitting layer 113 may be a single layer or include a plurality of layers containing different light-emitting substances.

Examples of a material which can be used as a fluorescent light-emitting substance in the light-emitting layer 113 are as follows. Fluorescent substances other than those given below can also be used.

Examples of the fluorescent substance are 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9-phenyl-9H-fluoren-9-yl)phenyl]-N,N'-diphenyl-pyrene-1,6-diamine (abbreviation: 1,6FLPAPrn), N,N'-bis(3-methylphenyl)-N,N'-bis[3-(9-phenyl-9H-fluoren-9-yl)phenyl]-pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chhrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2- methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{ 2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and the like. Condensed aromatic diamine compounds typified by pyrenediamine compounds such as 1,6FLPAPrn and 1,6mMemFLPAPm are preferable because of their high hole-trapping properties, high emission efficiency, and high reliability.

Examples of a material which can be used as a phosphorescent light-emitting substance in the light-emitting layer 113 are as follows.

The examples include organometallic iridium complexes having 4H-triazole skeletons, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-4H-1,2,4-triazolato]iridium(III) (abbreviation: [Ir(iPrptz-3b)$_3$]); organometallic iridium complexes having 1H-triazole skeletons, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic iridium complexes having imidazole skeletons, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIracac). These are compounds emitting blue phosphorescent light and have an emission peak at 440 nm to 520 nm.

Other examples include organometallic iridium complexes having pyrimidine skeletons, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having pyrazine skeletons, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having pyridine skeletons, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and rare earth metal complexes such as tris(acetylacetonato)(monophenanthroline)terbium(III) (abbreviation: [Tb(acac)$_3$(Phen)]). These are mainly compounds emitting green phosphorescent light and have an emission peak at 500 nm to 600 nm. Note that organometallic iridium complexes having pyrimidine skeletons have distinctively high reliability and emission efficiency and thus are especially preferable.

Other examples include organometallic iridium complexes having pyrimidine skeletons, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(d1npm)$_2$(dpm)]); organometallic iridium complexes having pyrazine skeletons, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having pyridine skeletons, such as tris(1-phenylisoquinolinato-N,C$^{2'}$)iridium(III) (abbreviation: [Ir(piq)$_3$]) and bis(1-phenylisoquinolinato-N,C$^{2'}$) iridium(III) acetylacetonate (abbreviation: [Ir(piq)$_2$(acac)]); platinum complexes such as 2,3,7,8,12,13,17,18-octaethyl-21H,23H-porphyrin platinum (II) (abbreviation: PtOEP); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]). These are compounds emitting red phosphorescent light and have an emission peak at 600 nm to 700 nm. Further, organometallic iridium complexes having pyrazine skeletons can provide red light emission with favorable chromaticity.

As well as the above phosphorescent compounds, a variety of phosphorescent light-emitting substances may be selected and used.

As a material exhibiting TADF, materials given below can be used. A fullerene, a derivative thereof, an acridine derivative such as proflavine, and eosin can be given. Further, a metal-containing porphyrin, such as a porphyrin containing magnesium (Mg), zinc (Zn), cadmium (Cd), tin (Sn), platinum (Pt), indium (In), or palladium (Pd) can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$(OEP)), which are shown in the following structural formulae.

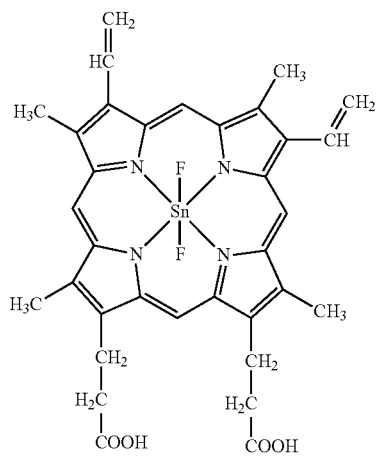

SnF$_2$(Proto IX)

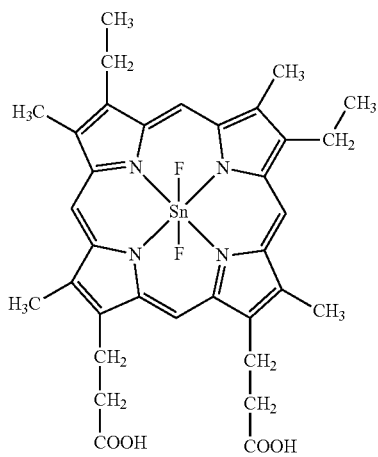

SnF$_2$(Meso IX)

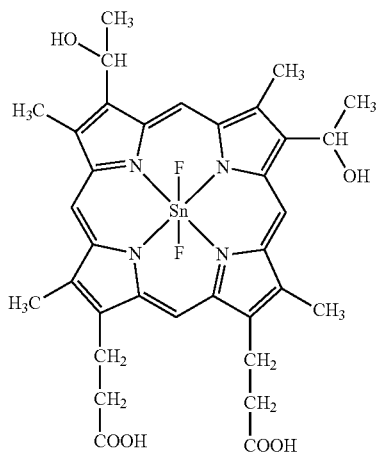

SnF$_2$(Hemato IX)

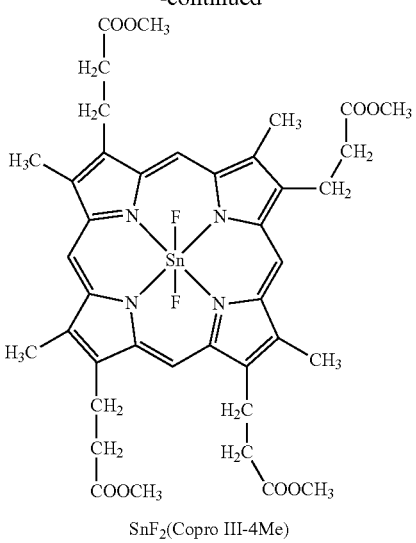

SnF$_2$(Copro III-4Me)

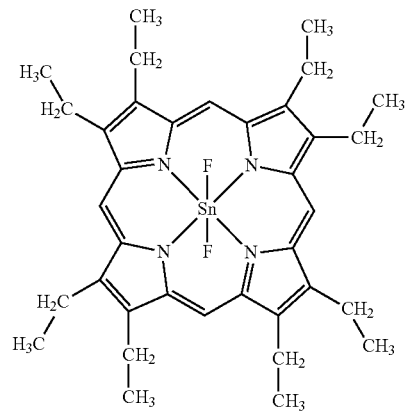

SnF$_2$(OEP)

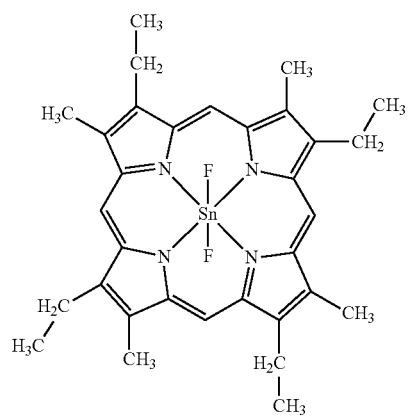

SnF$_2$(Etio I)

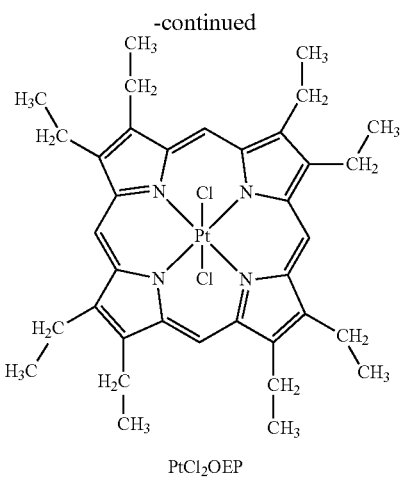

PtCl₂OEP

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-a]charbazol-11-yl)-1,3,5-triazine (PIC-TRZ) shown in the following structural formula, can be used. The heterocyclic compound is preferably used because of the π-electron rich heteroaromatic ring and the π-electron deficient heteroaromatic ring, for which the electron-transport property and the hole-transport property are high. Note that a substance in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both high and the difference between the $S_1$ level and the $T_1$ level becomes small.

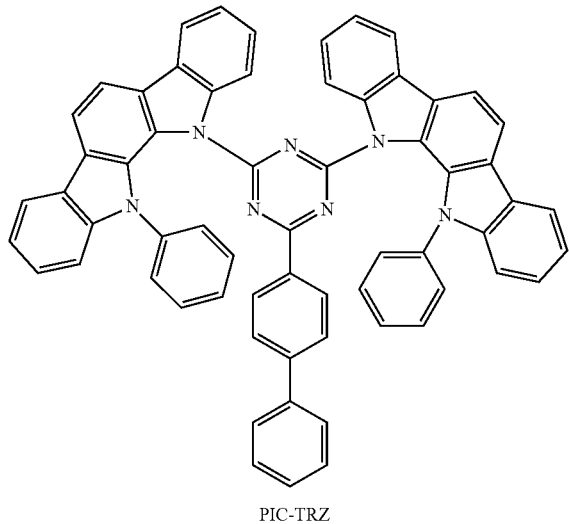 [SMILES: c1ccc(-c2ccc(-c3nc(-n4c5ccccc5c5ccc6c7ccccc7n(-c7ccccc7)c6c54)nc(-n4c5ccccc5c5ccc6c7ccccc7n(-c7ccccc7)c6c54)n3)cc2)cc1]

PIC-TRZ

As a host material of the light-emitting layer, the organic compound of one embodiment of the present invention, which is represented by any of the above general formulae (G1) to (G5), is preferably used.

Because of its favorable carrier-transport property, the above organic compound having the above-described structure enables a light-emitting element with low drive voltage and high emission efficiency to be obtained easily.

Furthermore, the organic compound has a high triplet excitation level. The organic compound is therefore preferably used especially as a light-emitting substance in a light-emitting element containing a phosphorescent substance or a TADF material, in which case the triplet energy can be effectively converted into luminescence. The organic compound is preferably used especially for a light-emitting element exhibiting green to blue phosphorescence.

In addition, the organic compound has high heat resistance and therefore enables a light-emitting element with high heat resistance to be fabricated.

In the case where the above organic compound is not used as the host material, a variety of carrier-transport materials can be used instead of the organic compound.

Examples of the material having an electron-transport property are a metal complex such as bis(10-hydroxybenzo[h]quinolinato)beryllium(II) (abbreviation: BeBq₂), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ); a heterocyclic compound having a polyazole skeleton such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II); a heterocyclic compound having a diazine skeleton such as 2-[3-(dibenzothiophen-4-yl)phenyl]dibenzo[f,h]quinoxaline (abbreviation: 2mDBTP-DBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2Pm-II); and a heterocyclic compound having a pyridine skeleton such as 3,5-bis[3-(9H-carbazol-9-yl)phenyl]pyridine (abbreviation: 35DCzPPy) or 1,3,5-tri[3-(3-pyridyl)-phenyl]benzene (abbreviation: TmPyPB). Among the above materials, a heterocyclic compound having a diazine skeleton and a heterocyclic compound having a pyridine skeleton have high reliability and are thus preferable. Specifically, a heterocyclic compound having a diazine skeleton has a high electron-transport property to contribute to a reduction in drive voltage.

Examples of the material having a hole-transport property include a compound having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]-fluoren-2- amine (abbreviation: PCBAF), or N-phenyl-N-[4-(9-phenyl-9H-carbazol-3-yl)phenyl]-spiro-9,9'-bifluoren-2-amine (abbreviation: PCBASF); a compound having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); and a compound having a furan skeleton such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II). Among the above materials, a compound having an aromatic amine skeleton and a compound having a carbazole skeleton are preferable because these compounds are highly reliable and have high hole-transport properties to contribute to a reduction in drive voltage. Hole-transport materials can be selected from a variety of substances as well as from the hole-transport materials given above.

Note that the host material may be a mixture of a plurality of kinds of substances, and in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

These mixed host materials may form an exciplex. When a combination of these materials is selected so as to form an exciplex that exhibits light emission whose wavelength overlaps the wavelength of a lowest-energy-side absorption band of the phosphorescent substance or the TADF material, energy is transferred smoothly and light emission can be obtained efficiently. Such a combination is preferable in that drive voltage can be reduced.

The light-emitting layer 113 having the above-described structure can be formed by co-evaporation by a vacuum evaporation method, or an inkjet method, a spin coating method, a dip coating method, or the like using a mixed solution.

The electron-transport layer 114 is a layer that contains a substance having an electron-transport property. As the substance having an electron-transport property, it is possible to use any of the above-listed materials having an electron-transport property which can be used as a host material. The electron-transport layer 114 may be a single layer or a double layered structure including a first electron-transport layer 114n and a second electron-transport layer 114m described in FIG. 1A.

Between the electron-transport layer and the light-emitting layer, a layer that controls transport of electron carriers may be provided. This is a layer formed by addition of a small amount of a substance having a high electron-trapping property to the aforementioned material having a high electron-transport property, and the layer is capable of adjusting carrier balance by retarding transport of electron carriers. Such a structure is very effective in preventing a problem (such as a reduction in element lifetime) caused when electrons pass through the light-emitting layer.

In addition, the electron-injection layer 115 may be provided in contact with the second electrode 102 between the electron-transport layer 114 and the second electrode 102. For the electron-injection layer 115, an alkali metal, an alkaline earth metal, or a compound thereof, such as lithium fluoride (LiF), cesium fluoride (CsF), or calcium fluoride ($CaF_2$), can be used. For example, a layer that is formed using a substance having an electron-transport property and contains an alkali metal, an alkaline earth metal, or a compound thereof can be used. In addition, an electride may be used for the electron-injection layer 115. Examples of the electride include a substance in which electrons are added at high concentration to calcium oxide-aluminum oxide. Note that a layer that is formed using a substance having an electron-transport property and contains an alkali metal or an alkaline earth metal is preferably used as the electron-injection layer 115, in which case electron injection from the second electrode 102 is efficiently performed.

For the second electrode 102, any of metals, alloys, electrically conductive compounds, and mixtures thereof which have a low work function (specifically, a work function of 3.8 eV or less) or the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys thereof (e.g., MgAg and AlLi), rare earth metals such as europium (Eu) and ytterbium (Yb), alloys thereof, and the like. However, when the electron-injection layer is provided between the second electrode 102 and the electron-transport layer 114, for the second electrode 102, any of a variety of conductive materials such as Al, Ag, ITO, or indium oxide-tin oxide containing silicon or silicon oxide can be used regardless of the work function. Films of these electrically conductive materials can be formed by a sputtering method, an inkjet method, a spin coating method, or the like.

Any of a variety of methods can be used to form the EL layer 103 regardless whether it is a dry process or a wet process. For example, a vacuum evaporation method, an inkjet method, a spin coating method, or the like may be used. Different formation methods may be used for the electrodes or the layers.

In addition, the electrode may be formed by a wet method using a sol-gel method, or by a wet method using paste of a metal material. Alternatively, the electrode may be formed by a dry method such as a sputtering method or a vacuum evaporation method.

Light emission from the light-emitting element is extracted out through one or both of the first electrode 101 and the second electrode 102. Therefore, one or both of the first electrode 101 and the second electrode 102 is formed as a light-transmitting electrode.

Note that this embodiment can be combined with any of the other embodiments as appropriate.

Next, an embodiment of a light-emitting element with a structure in which a plurality of light-emitting units are stacked (hereinafter this type of light-emitting element is also referred to as a stacked element) is described with reference to FIG. 1B. This light-emitting element includes, between a first electrode and a second electrode, a plurality of light-emitting units with a charge generation layer interposed therebetween. One light-emitting unit has the same structure as the EL layer 103 illustrated in FIG. 1A. In other words, the light-emitting element illustrated in FIG. 1A includes a single light-emitting unit, and the light-emitting element illustrated in FIG. 1B includes a plurality of light-emitting units.

Figure 1B:
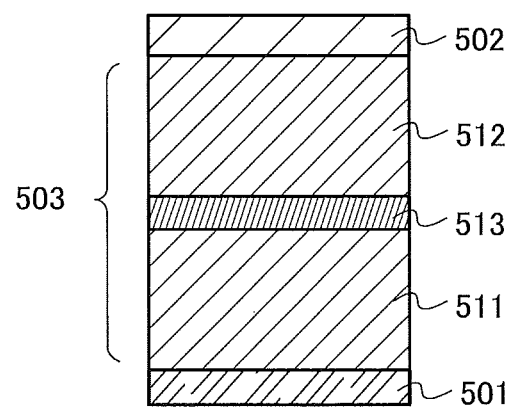

In FIG. 1B, an EL layer 503 including a stack of a first light-emitting unit 511, a charge generation layer 513, and a second light-emitting unit 512 is provided between a first electrode 501 and a second electrode 502. The first electrode 501 and the second electrode 502 correspond, respectively, to the first electrode 101 and the second electrode 102 illustrated in FIG. 1A, and can be formed using the materials given in the description for FIG. 1A. Furthermore, the first light-emitting unit 511 and the second light-emitting unit 512 may have the same structure or different structures.

The charge generation layer 513 contains a composite material of an organic compound and a metal oxide. As this composite material of an organic compound and a metal oxide, the composite material that can be used for the hole-injection layer 111 illustrated in FIG. 1A can be used. Since the composite material of an organic compound and a metal oxide is superior in carrier-injection property and carrier-transport property, low-voltage driving or low-current driving can be realized. Note that when a surface of a light-emitting unit on the anode side is in contact with the charge generation layer, the charge generation layer can also serve as a hole-injection layer of the light-emitting unit; thus, a hole-injection layer does not need to be formed in the light-emitting unit.

Note that the charge generation layer 513 may be formed by stacking a layer containing the above composite material and a layer containing another material. For example, the charge generation layer 513 may be formed by stacking the layer containing the composite material and a layer containing a compound selected from electron-donating substances and a compound having a high electron-transport property, or by stacking a layer containing the composite material of an organic compound and a metal oxide and a transparent conductive film.

An electron-injection buffer layer may be provided between the charge-generation layer 513 and the light-emitting unit on the anode side of the charge-generation layer. The electron-injection buffer layer is a stack of a very thin alkali metal layer and an electron-relay layer containing a substance having an electron-transport property. The very thin alkali metal layer corresponds to the electron-injection layer 115 and has a function of lowering an electron injection barrier. The electron-relay layer has a function of preventing an interaction between the alkali metal layer and the charge-generation layer and smoothly transferring electrons.

The LUMO level of the substance having an electron-transport property which is contained in the electron-relay layer is set to be between the LUMO level of an substance having an acceptor property in the charge-generation layer 513 and the LUMO level of a substance contained in a layer in contact with the electron-injection buffer layer in the light-emitting unit on the anode side. As a specific value of the energy level, the LUMO level of the substance having an electron-transport property which is contained in the electron-relay layer is preferably greater than or equal to −5.0 eV, more preferably greater than or equal to −5.0 eV and less than or equal to −3.0 eV. Note that as the substance having an electron-transport property which is contained in the electron-relay layer, a metal complex having a metal-oxygen bond and an aromatic ligand or a phthalocyanine-based material is preferably used.

The light-emitting element having two light-emitting units is described with reference to FIG. 1B; however, the present invention can be similarly applied to a light-emitting element in which three or more light-emitting units are stacked. With a plurality of light-emitting units partitioned by the charge-generation layer between a pair of electrodes, it is possible to provide an element which can emit light with high luminance with the current density kept low and has a long lifetime. A light-emitting device that can be driven at a low voltage and has low power consumption can be realized.

Furthermore, when emission colors of the light-emitting units are made different, light emission having a desired color can be obtained from the light-emitting element as a whole. For example, it is easy to enable a light-emitting element having two light-emitting units to emit white light as the whole element when the emission colors of the first light-emitting unit are red and green and the emission color of the second light-emitting unit is blue.

(Light-Emitting Device)

A light-emitting device of one embodiment of the present invention is described using FIGS. 2A and 2B. Note that FIG. 2A is a top view illustrating the light-emitting device and FIG. 2B is a cross-sectional view of FIG. 2A taken along lines A-B and C-D. This light-emitting device includes a driver circuit portion (source line driver circuit) 601, a pixel portion 602, and a driver circuit portion (gate line driver circuit) 603, which can control light emission of a light-emitting element and illustrated with dotted lines. A reference numeral 604 denotes a sealing substrate; 605, a sealing material; and a portion surrounded by the sealing material 605 is a space 607.

Reference numeral 608 denotes a wiring for transmitting signals to be input to the source line driver circuit 601 and the gate line driver circuit 603 and receiving signals such as a video signal, a clock signal, a start signal, and a reset signal from an flexible printed circuit (FPC) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure will be described with reference to FIG. 2B. The driver circuit portion and the pixel portion are formed over an element substrate 610; the source line driver circuit 601, which is a driver circuit portion, and one of the pixels in the pixel portion 602 are illustrated here.

As the source line driver circuit 601, a CMOS circuit in which an n-channel FET 623 and a p-channel FET 624 are combined is formed. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit is not necessarily formed over the substrate, and the driver circuit can be formed outside, not over the substrate.

The pixel portion 602 includes a plurality of pixels including a switching FET 611, a current controlling FET 612, and a first electrode 613 electrically connected to a drain of the current controlling FET 612. One embodiment of the present invention is not limited to the structure. The pixel portion 602 may include three or more FETs and a capacitor in combination.

The kind and crystallinity of a semiconductor used for the FETs is not particularly limited; an amorphous semiconductor or a crystalline semiconductor may be used. Examples of the semiconductor used for the FETs include Group IV semiconductors (e.g., silicon), Group III semiconductors (e.g., gallium), compound semiconductors, oxide semiconductors, and organic semiconductors. Oxide semiconductors are particularly preferable. Examples of the oxide semiconductor include an In—Ga oxide and an In-M-Zn oxide (M is Al, Ga, Y, Zr, La, Ce, or Nd). Note that an oxide semiconductor that has an energy gap of 2 eV or more, preferably 2.5 eV or more, further preferably 3 eV or more is preferably used, in which case the off-state current of the transistors can be reduced.

Note that to cover an end portion of the first electrode 613, an insulator 614 is framed. The insulator 614 can be formed using a positive photosensitive acrylic resin film here.

An EL layer 616 and a second electrode 617 are formed over the first electrode 613. The first electrode 613, the EL layer 616, and the second electrode 617 correspond, respectively, to the first electrode 101, the EL layer 103, and the second electrode 102 in FIG. 1A or to the first electrode 501, the EL layer 503, and the second electrode 502 in FIG. 1B.

The EL layer 616 preferably includes the organic compound represented by any of the above general formulae (G1) to (G5).

The sealing substrate 604 is attached to the element substrate 610 with the sealing material 605, so that a light-emitting element 618 is provided in the space 607 surrounded by the element substrate 610, the sealing substrate 604, and the sealing material 605. The space 607 may be filled with filler, or may be filled with an inert gas (such as nitrogen or argon), or the sealing material 605. It is preferable that the sealing substrate 604 be provided with a recessed portion and a drying agent be provided in the recessed portion, in which case deterioration due to influence of moisture can be suppressed.

An epoxy-based resin or glass frit is preferably used for the sealing material 605. It is preferable that such a material do not transmit moisture or oxygen as much as possible. As the element substrate 610 and the sealing substrate 604, a glass substrate, a quartz substrate, or a plastic substrate formed of fiber reinforced plastic (FRP), polyvinyl fluoride) (PVF), polyester, or acrylic can be used.

FIGS. 3A and 3B each illustrate an example of a light-emitting device in which full color display is achieved by formation of a light-emitting element exhibiting white light emission and with the use of coloring layers (color filters) and the like. In FIG. 3A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, an EL layer 1028, a second electrode 1029 of the light-emitting elements, a sealing substrate 1031, a sealing material 1032, and the like are illustrated.

In FIG. 3A, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer may be covered with an overcoat layer 1036. In FIG. 3A, light emitted from part of the light-emitting layer does not pass through the coloring layers, while light emitted from the other part of the light-emitting layer passes through the coloring layers. Since light which does not pass through the coloring layers is white and light which passes through any one of the coloring layers is red, blue, or green, an image can be displayed using pixels of the four colors.

FIG. 3B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 4:
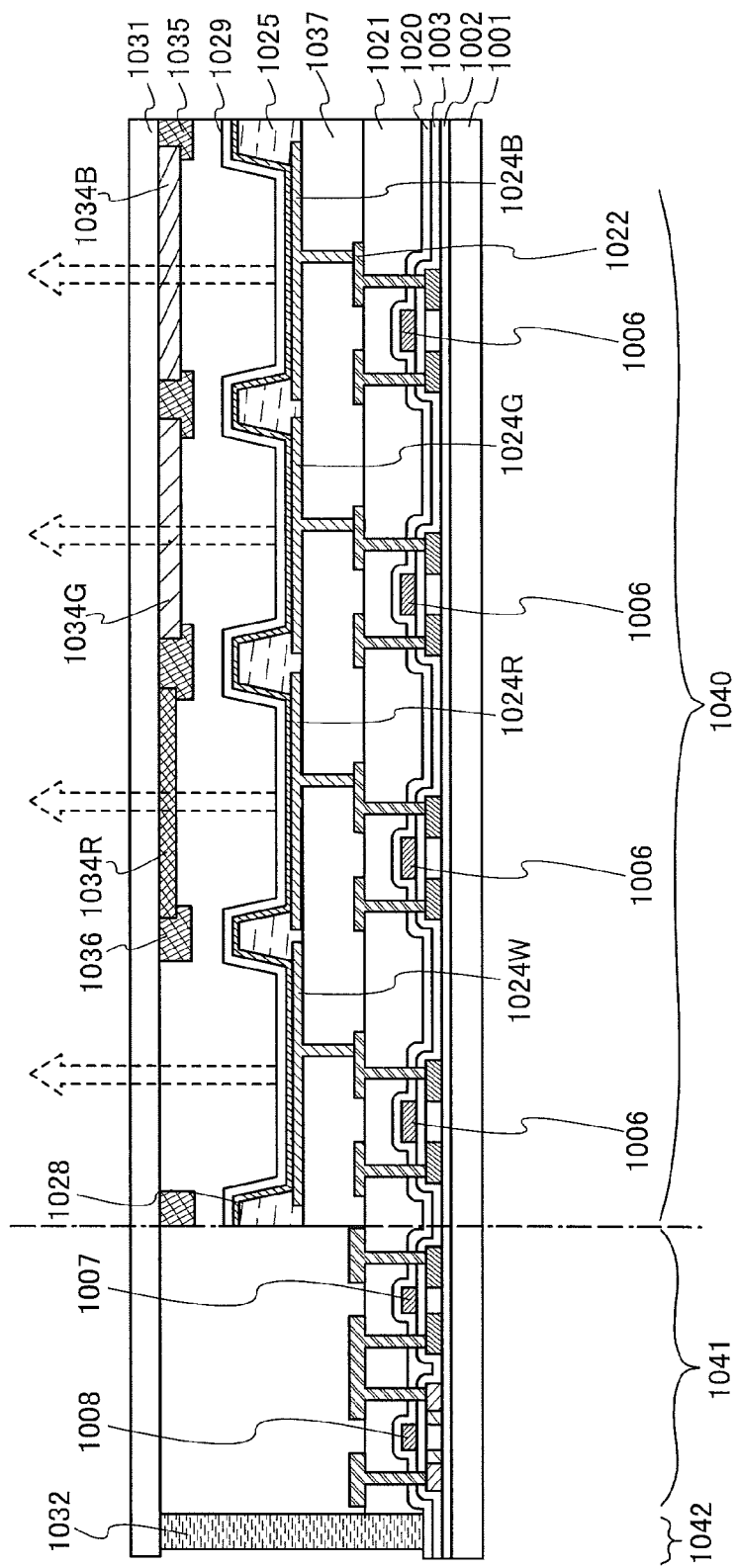
FIG. 4 is a conceptual view of an active matrix light-emitting device.

The above-described light-emitting device is a light-emitting device having a structure in which light is extracted from the substrate 1001 side where the FETs are fainted (a bottom emission structure), but may be a light-emitting device having a structure in which light is extracted from the sealing substrate 1031 side (a top emission structure). FIG. 4 is a cross-sectional view of a light-emitting device having a top emission structure. In this case, a substrate which does not transmit light can be used as the substrate 1001. The process up to the step of forming a connection electrode which connects the FET and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film 1021, and can alternatively be formed using any of other various materials.

The first electrodes 1024W, 1024R, 1024G, and 1024B of the light-emitting elements each serve as an anode here, but may serve as a cathode. Further, in the case of a light-emitting device having a top emission structure as illustrated in FIG. 4, the first electrodes are preferably reflective electrodes. The EL layer 1028 is formed to have a structure similar to the structure of the EL layer 103 in FIG. 1A or the EL layer 503 in FIG. 1B, with which white light emission can be obtained.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (black matrix) 1035 which is positioned between pixels. The coloring layers (the red coloring layer 1034R, the green coloring layer 1034G, and the blue coloring layer 1034B) and the black layer (black matrix) 1035 may be covered with an overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue may be performed.

Figure 5A:
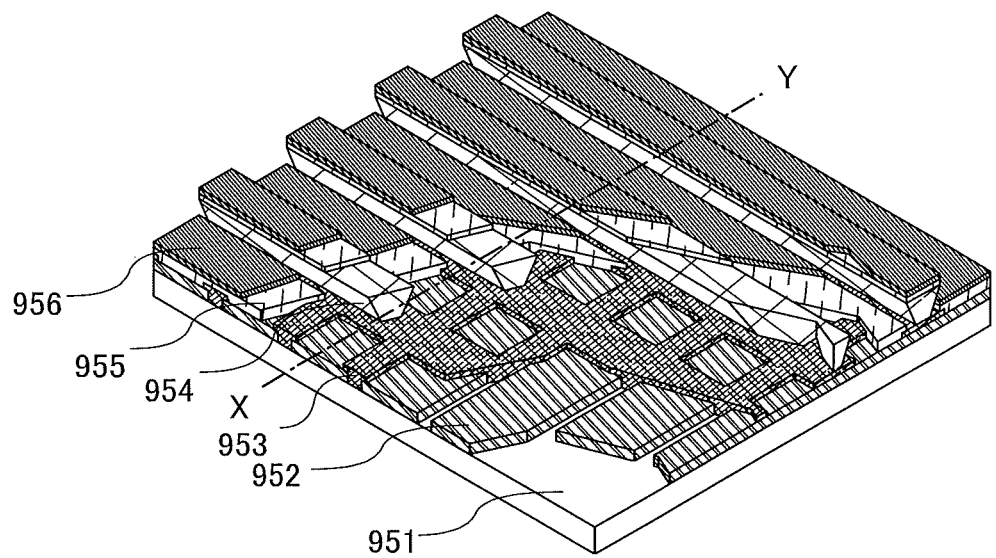
FIGS. 5A and 5B are conceptual views of a passive matrix light-emitting device.
Figure 5B:
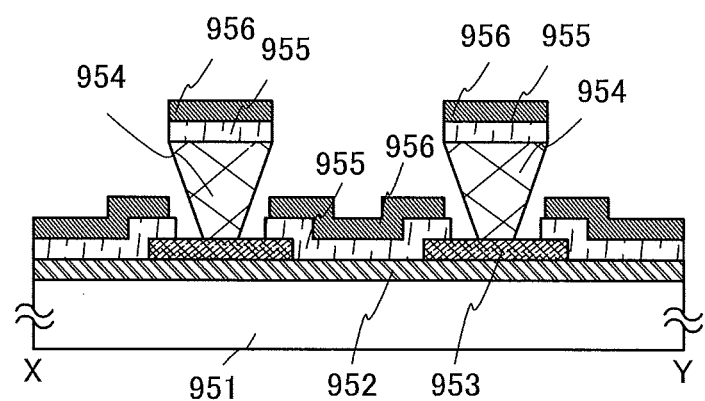

FIGS. 5A and 5B illustrate a passive matrix light-emitting device which is one embodiment of the present invention. FIG. 5A is a perspective view of the light-emitting device, and FIG. 5B is a cross-sectional view of FIG. 5A taken along line X-Y. In FIGS. 5A and 5B, an EL layer 955 is provided between an electrode 952 and an electrode 956 over a substrate 951. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition layer 954 is trapezoidal, and the lower side (a side in contact with the insulating layer 953, which is one of a pair of parallel sides of the trapezoidal cross section) is shorter than the upper side (a side not in contact with the insulating layer 953, which is the other one of the pair of parallel sides). The partition layer 954 thus provided can prevent defects in the light-emitting element due to static electricity or others.

Since many minute light-emitting elements arranged in a matrix can each be controlled with the FETs formed in the pixel portion, the above-described light-emitting device can be suitably used as a display device for displaying images.
(Lighting Device)

Figure 6A:
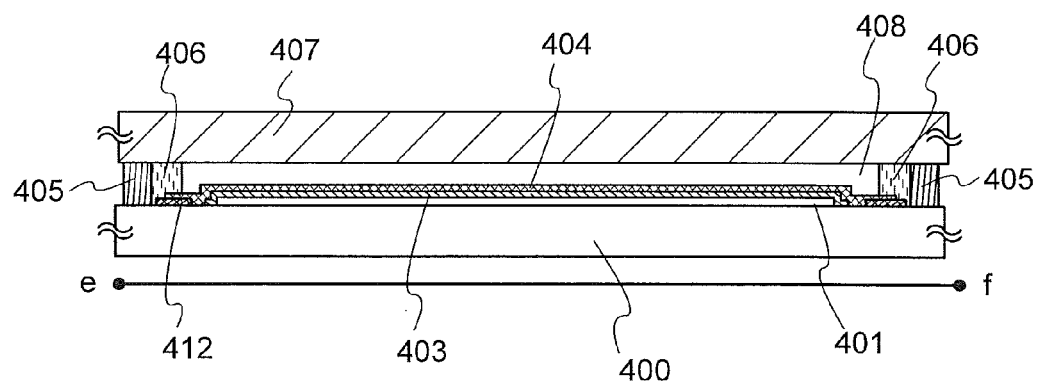
FIGS. 6A and 6B illustrate a lighting device.
Figure 6B:
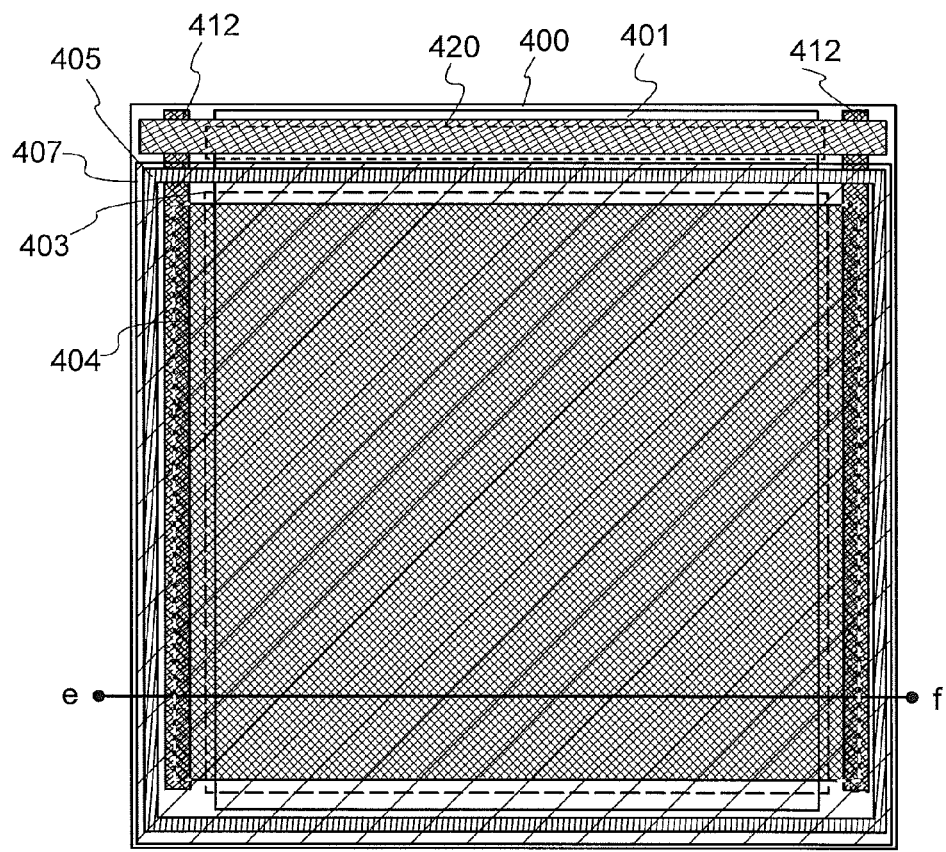

A lighting device which is one embodiment of the present invention is described with reference to FIGS. 6A and 6B. FIG. 6B is a top view of the lighting device, and FIG. 6A is a cross-sectional view of FIG. 6A taken along line e-f.

In the lighting device, a first electrode 401 is formed over a substrate 400 which is a support and has a light-transmitting property. The first electrode 401 corresponds to the first electrode 101 in FIGS. 1A and 1B. When light is extracted through the first electrode 401 side, the first electrode 401 is formed using a material having a light-transmitting property.

A pad 412 for applying a voltage to a second electrode 404 is provided over the substrate 400.

An EL layer 403 is formed over the first electrode 401. The EL layer 403 corresponds to, for example, the EL layer 103 in FIG. 1A or the EL layer 503 in FIG. 1B. Refer to the descriptions for the structure.

The second electrode 404 is formed to cover the EL layer 403. The second electrode 404 corresponds to the second electrode 102 in FIG. 1A. The second electrode 404 is formed using a material having high reflectance when light is extracted through the first electrode 401 side. The second electrode 404 is connected to the pad 412, whereby a voltage is applied.

A light-emitting element is formed with the first electrode 401, the EL layer 403, and the second electrode 404. The substrate 400 provided with the light-emitting element is fixed to a sealing substrate 407 with sealing materials 405 and 406 and sealing is performed, whereby the lighting device is completed. It is possible to use only either the sealing material 405 or the sealing material 406. In addition, the inner sealing material 406 (not shown in FIG. 6B) can be mixed with a desiccant, whereby moisture is adsorbed and the reliability is increased.

When parts of the pad 412 and the first electrode 401 are extended to the outside of the sealing materials 405 and 406, the extended parts can serve as external input terminals. An IC chip 420 mounted with a converter or the like may be provided over the external input terminals.
(Electronic Device)

Examples of an electronic device which is one embodiment of the present invention are described. Examples of the electronic device are television devices (also referred to as TV or television receivers), monitors for computers and the like, cameras such as digital cameras and digital video cameras, digital photo frames, mobile phones (also referred to as cell phones or mobile phone devices), portable game machines, portable information terminals, audio playback devices, large game machines such as pachinko machines, and the like.

FIG. 7A illustrates an example of a television device. In the television device, a display portion 7103 is incorporated in a housing 7101. In addition, here, the housing 7101 is supported by a stand 7105. Images can be displayed on the display portion 7103, and in the display portion 7103, light-emitting elements are arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

FIG. 7B1 illustrates a computer, which includes a main body 7201, a housing 7202, a display portion 7203, a keyboard 7204, an external connection port 7205, a pointing device 7206, and the like. Note that this computer is manufactured by using light-emitting elements arranged in a matrix in the display portion 7203, which are the same as that described above. The computer illustrated in FIG. 7B 1 may have a structure illustrated in FIG. 7B2. A computer illustrated in FIG. 7B2 is provided with a second display portion 7210 instead of the keyboard 7204 and the pointing device 7206. The second display portion 7210 is a touch screen, and input can be performed by operation of display for input on the second display portion 7210 with a finger or a dedicated pen. The second display portion 7210 can also display images other than the display for input. The display portion 7203 may be also a touch screen. Connecting the two screens with a hinge can prevent troubles; for example, the screens can be prevented from being cracked or broken while the computer is being stored or carried.

FIG. 7C illustrates a portable game machine, which includes two housings, a housing 7301 and a housing 7302, which are connected with a joint portion 7303 so that the portable game machine can be opened or folded. The housing 7301 incorporates a display portion 7304 including light-emitting elements and arranged in a matrix, and the housing 7302 incorporates a display portion 7305. In addition, the portable game machine illustrated in FIG. 7D includes a speaker portion 7306, a storage medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. The portable game machine illustrated in FIG. 7D has a function of reading out a program or data stored in a storage medium to display it on the display portion, and a function of sharing information with another portable game machine by wireless communication. The portable game machine illustrated in FIG. 7D can have a variety of functions without limitation to the above.

FIG. 7D illustrates an example of a mobile phone. The mobile phone is provided with a display portion 7402 incorporated in a housing 7401, operation buttons 7403, an external connection port 7404, a speaker 7405, a microphone 7406, and the like. Note that the mobile phone has the display portion 7402 including light-emitting elements and arranged in a matrix.

When the display portion 7402 of the mobile phone illustrated in FIG. 7D is touched with a finger or the like, information can be input into the mobile phone. In this case, operations such as making a call and creating an e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating e-mail, a text input mode mainly for inputting text is selected for the display portion 7402 so that text displayed on a screen can be inputted. In this case, it is preferable to display a keyboard or number buttons on almost the entire screen of the display portion 7402.

When a detection device including a sensor such as a gyroscope or an acceleration sensor for detecting inclination is provided inside the mobile phone, screen display of the display portion 7402 can be automatically changed by determining the orientation of the mobile phone (whether the mobile phone is placed horizontally or vertically).

The screen modes are switched by touch on the display portion 7402 or operation with the operation buttons 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by the display portion 7402 while in touch with the palm or the finger, whereby personal authentication can be performed. Further, by providing a backlight or a sensing light source which emits near-infrared light in the display portion, an image of a finger vein, a palm vein, or the like can be taken.

Note that in the above electronic devices, any of the structures described in this specification can be combined as appropriate.

Furthermore, each display portion preferably includes a light-emitting element including the organic compound represented by any of the above general formulae (G1) to (G5). Since the light-emitting element can be a light-emitting element with high emission efficiency, the electronic device can have low power consumption.

Figure 8:
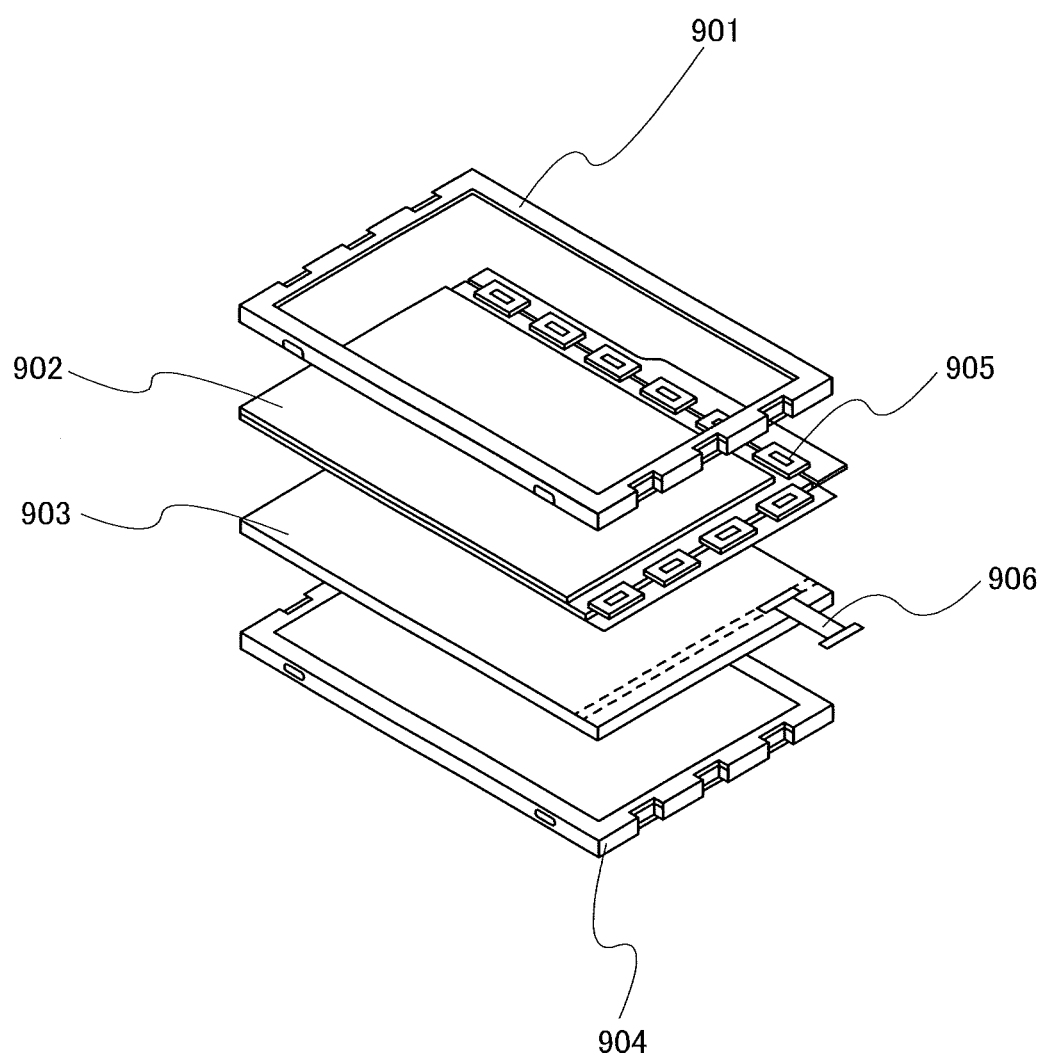
FIG. 8 illustrates a light source device.

FIG. 8 illustrates an example of a liquid crystal display device including the light-emitting element. The liquid crystal display device illustrated in FIG. 8 includes a housing 901, a liquid crystal layer 902, a backlight unit 903, and a housing 904. The liquid crystal layer 902 is connected to a driver IC 905. The light-emitting element is used for the backlight unit 903, to which current is supplied through a terminal 906.

As the light-emitting element, a light-emitting element including the organic compound represented by any of the above general formulae (G1) to (G5) is preferably used. By including the light-emitting element, the backlight of the liquid crystal display device can have low power consumption.

Figure 9:
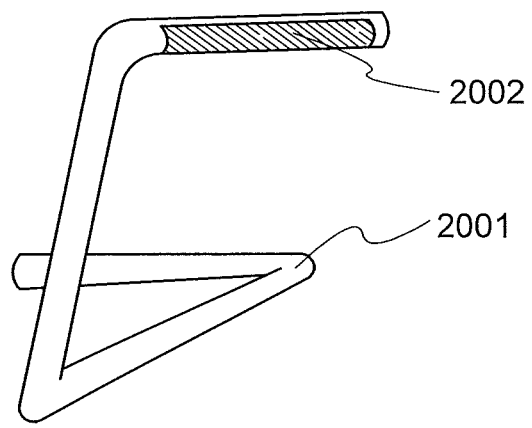
FIG. 9 illustrates a lighting device.

FIG. 9 illustrates an example of a desk lamp which is one embodiment of the present invention. The desk lamp illustrated in FIG. 9 includes a housing 2001 and a light source 2002, and a lighting device including a light-emitting element is used as the light source 2002.

Figure 10:
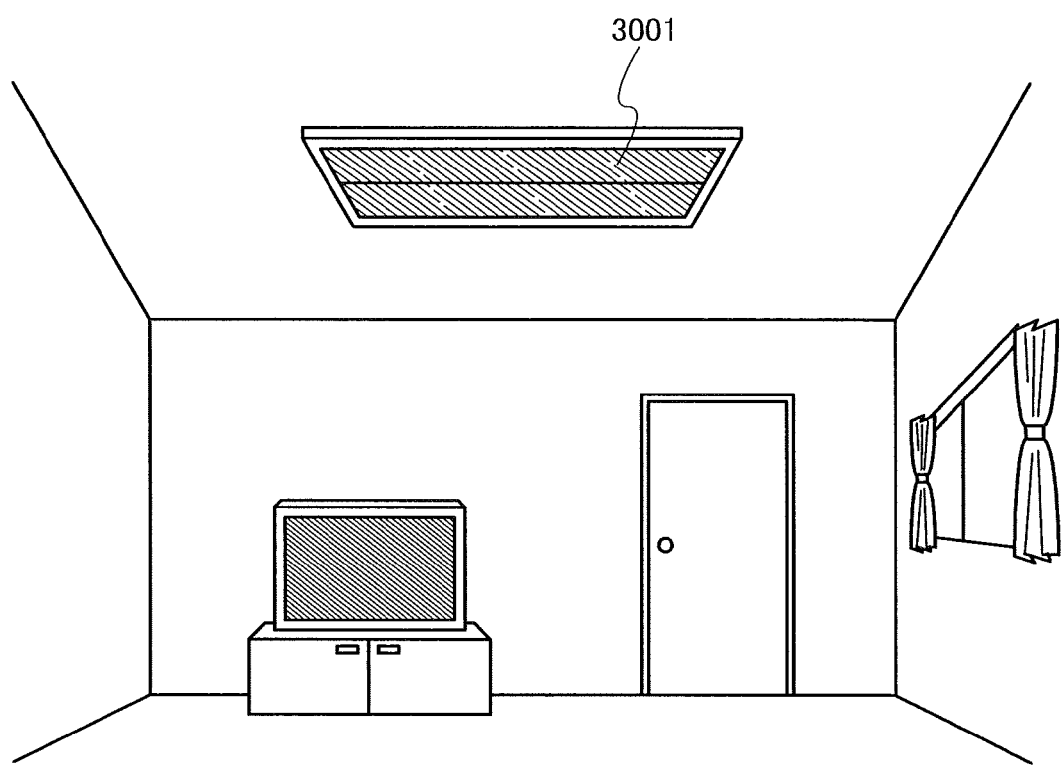
FIG. 10 illustrates a lighting device.

FIG. 10 illustrates an example of an indoor lighting device 3001. The lighting device 3001 preferably includes a light-emitting element including an organic compound in which heteroaromatic groups each including two pyridine rings are bonded to the 2- and 8-positions of dibenzofuran. Since the organic compound is a substance having a high carrier-transport property, the lighting device can have low power consumption.

Figure 11:
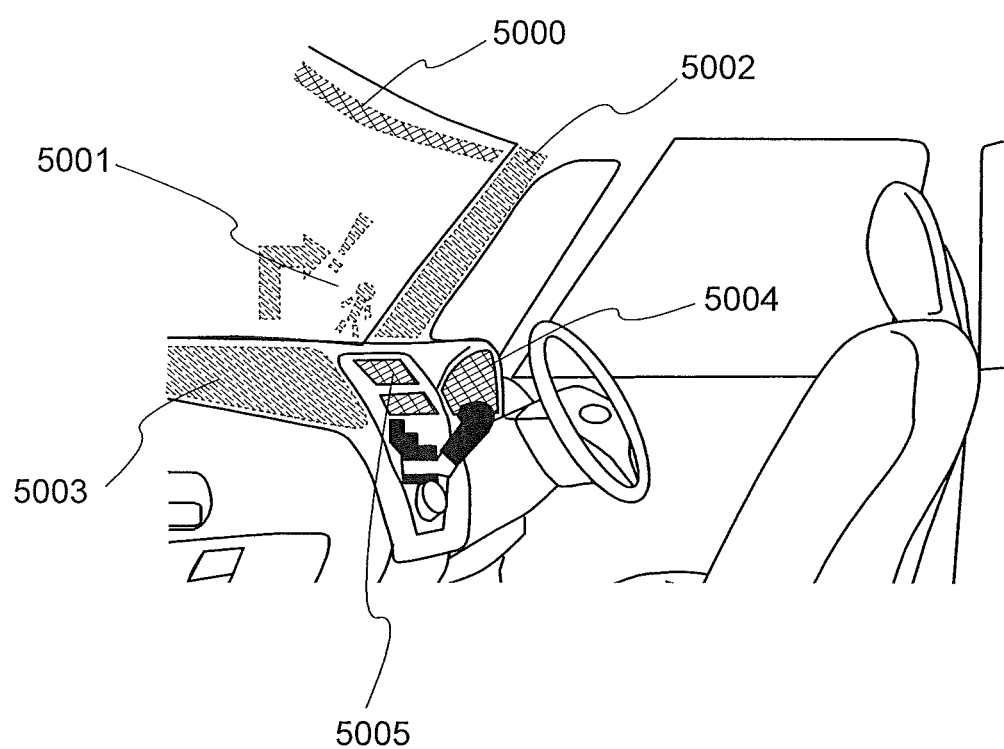
FIG. 11 illustrates in-vehicle display devices and lighting devices.

An automobile which is one embodiment of the present invention is illustrated in FIG. 11. In the automobile, light-emitting elements are used for a windshield and a dashboard. Display regions 5000 to 5005 are provided by using the light-emitting elements. The light-emitting elements preferably include the organic compound represented by any of the above general formulae (G1) to (G5), and can have low drive voltage by including the organic compound. This also suppresses power consumption of the display regions 5000 to 5005, showing suitability for use in an automobile.

The display regions 5000 and 5001 are provided in the automobile windshield including the light-emitting elements. When a first electrode and a second electrode are formed of electrodes having light-transmitting properties in these light-emitting elements, what is called a see-through display device, through which the opposite side can be seen, can be obtained. Such a see-through display device can be provided even in the automobile windshield, without hindering the vision. Note that in the case where a transistor for driving or the like is provided, a transistor having a light-transmitting property, such as an organic transistor using an organic semiconductor material or a transistor using an oxide semiconductor, is preferably used.

The display region 5002 is provided in a pillar portion using a light-emitting element. The display region 5002 can compensate for the view hindered by the pillar portion by showing an image taken by an imaging unit provided in the car body. Similarly, a display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation information, a speedometer, a tachometer, a mileage, a fuel meter, a gearshift indicator, and air-condition setting. The content or layout of the display can be changed freely by a user as appropriate. Note that such information can also be shown by the display regions 5000 to 5003. The display regions 5000 to 5005 can also be used as lighting devices.

Figure 12A:
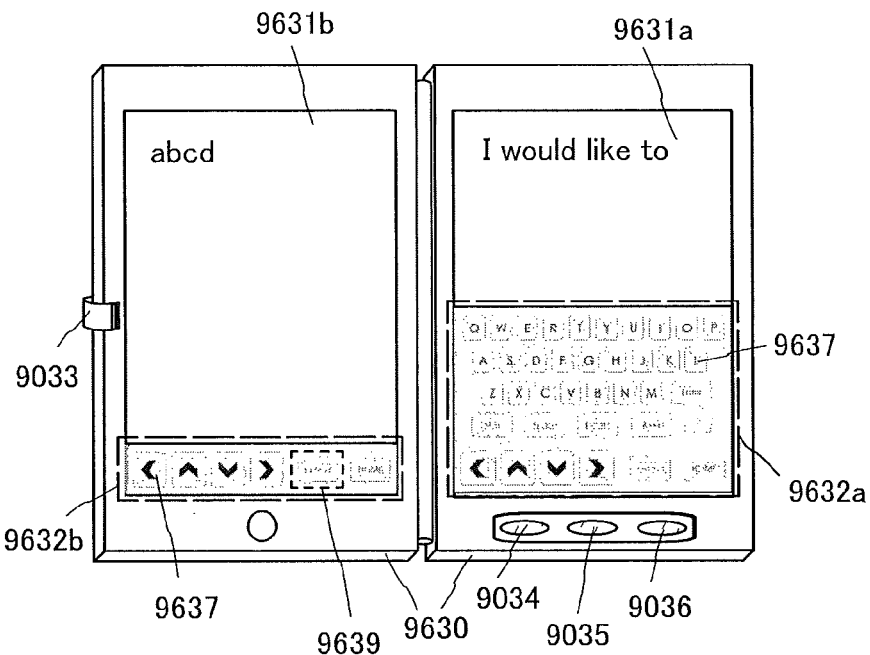
FIGS. 12A to 12C illustrate an electronic device.
Figure 12B:
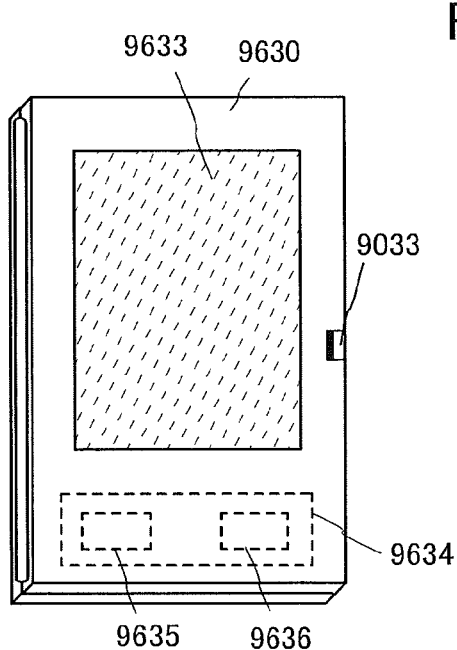

FIGS. 12A and 12B illustrate an example of a foldable tablet terminal. FIG. 12A illustrates the tablet terminal which is unfolded. The tablet terminal includes a housing 9630, a display portion 9631*a*, a display portion 9631*b*, a display mode switch 9034, a power switch 9035, a power-saving mode switch 9036, and a clasp 9033. Note that in the tablet terminal, one or both of the display portion 9631*a* and the display portion 9631*b* is/are formed using a light-emitting device which includes the above-described light-emitting element.

Part of the display portion 9631*a* can be a touchscreen region 9632*a* and data can be input when a displayed operation key 9637 is touched. Although half of the display portion 9631*a* has only a display function and the other half has a touchscreen function, one embodiment of the present invention is not limited to the structure. The whole display portion 9631*a* may have a touchscreen function. For example, a keyboard can be displayed on the entire region of the display portion 9631*a* so that the display portion 9631*a* is used as a touchscreen, and the display portion 9631*b* can be used as a display screen.

Like the display portion 9631*a*, part of the display portion 9631*b* can be a touchscreen region 9632*b*. When a switching button 9639 for showing/hiding a keyboard on the touchscreen is touched with a finger, a stylus, or the like, the keyboard can be displayed on the display portion 9631*b*.

Touch input can be performed in the touchscreen region 9632*a* and the touchscreen region 9632*b* at the same time.

The display mode switch 9034 can switch the display between portrait mode, landscape mode, and the like, and between monochrome display and color display, for example. The power-saving mode switch 9036 can control display luminance in accordance with the amount of external light in use of the tablet terminal sensed by an optical sensor incorporated in the tablet terminal. Another sensing device including a sensor such as a gyroscope or an acceleration sensor for sensing inclination may be incorporated in the tablet terminal, in addition to the optical sensor.

Although FIG. 12A illustrates an example in which the display portion 9631*a* and the display portion 9631*b* have the same display area, one embodiment of the present invention is not limited to the example. The display portion 9631*a* and the display portion 9631*b* may have different display areas and different display quality. For example, higher definition images may be displayed on one of the display portions 9631*a* and 9631*b*.

FIG. 12B illustrates the tablet terminal which is folded. The tablet terminal in this embodiment includes the housing 9630, a solar cell 9633, a charge and discharge control circuit 9634, a battery 9635, and a DCDC converter 9636. In FIG. 12B, a structure including the battery 9635 and the DCDC converter 9636 is illustrated as an example of the charge and discharge control circuit 9634.

Since the tablet terminal is foldable, the housing 9630 can be closed when the tablet terminal is not in use. As a result, the display portion 9631*a* and the display portion 9631*b* can be protected, thereby providing a tablet terminal with high endurance and high reliability for long-term use.

The tablet terminal illustrated in FIGS. 12A and 12B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar cell 9633 provided on a surface of the tablet terminal can supply power to the touchscreen, the display portion, a video signal processing portion, or the like. Note that a structure in which the solar cell 9633 is provided on one or both surfaces of the housing 9630 is preferable because the battery 9635 can be charged efficiently.

Figure 12C:
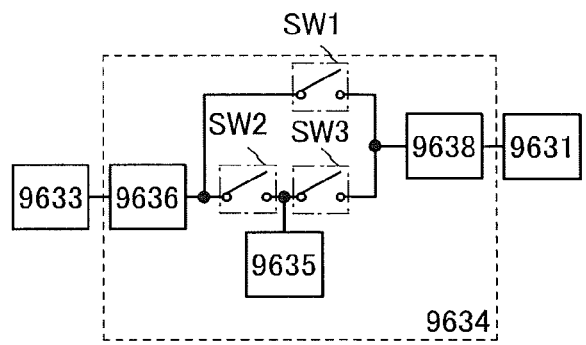

The structure and operation of the charge and discharge control circuit 9634 illustrated in FIG. 12B are described with reference to a block diagram of FIG. 12C. FIG. 12C illustrates the solar cell 9633, the battery 9635, the DCDC converter 9636, a converter 9638, switches SW1 to SW3, and a display portion 9631. The battery 9635, the DCDC converter 9636, the converter 9638, and the switches SW1 to SW3 correspond to the charge and discharge control circuit 9634 illustrated in FIG. 12B.

First, description is made on an example of the operation in the case where power is generated by the solar cell 9633 with the use of external light. The voltage of the power generated by the solar cell is raised or lowered by the DCDC converter 9636 so as to be voltage for charging the battery 9635. Then, when power from the solar cell 9633 is used for the operation of the display portion 9631, the switch SW1 is turned on and the voltage of the power is raised or lowered by the converter 9638 so as to be voltage needed for the display portion 9631. When images are not displayed on the display portion 9631, the switch SW1 is turned off and the switch SW2 is turned on so that the battery 9635 is charged.

Although the solar cell 9633 is described as an example of a power generation means, the power generation means is not particularly limited, and the battery 9635 may be charged by another power generation means such as a piezoelectric element or a thermoelectric conversion element (Peltier element). The battery 9635 may be charged by a non-contact power transmission module capable of performing charging by transmitting and receiving power wirelessly (without contact), or any of the other charge means used in combination, and the power generation means is not necessarily provided.

One embodiment of the present invention is not limited to the tablet terminal having the shape illustrated in FIGS. 12A to 12C as long as the display portion 9631 is included.

Example 1

In this example, a method of synthesizing 2,2'-(dibenzofuran-2,8-diyl)bis[4-(2-pyridyl)pyrimidine] (abbreviation: PyPm2DBF-01), which is an organic compound of one embodiment of the present invention, is described in detail.

Step 1: Synthesis of 2-Chloro-4-(2-pyridyl)pyrimidine

First, 6.0 g (22.4 mmol) of 2-pyridineboronic acid N-phenyldiethanolamine ester, 3.3 g (22.4 mmol) of 2,4-dichloropyrimidine, 9.5 g (44.7 mmol) of tripotassium phosphate, 0.785 g (1.1 mmol) of bis(triphenylphosphine)palladium(II) dichloride, and 2.1 g (11.1 mmol) of copper iodide were put into a 500-mL three-neck flask, and the air in the flask was replaced with nitrogen. To the mixture, 200 mL of dehydrated N,N-dimethylformamide was added. This mixture was degassed by being stirred under reduced pressure, and stirred under a nitrogen stream at 100° C. for 6.5 hours. After that, ethyl acetate and water were added to the obtained reaction solution, and the precipitated solid was removed by suction filtration. The obtained filtrate was separated into an aqueous layer and an organic layer, and extraction of the aqueous layer was performed. The solution obtained by the extraction and the organic layer were combined and washed with a saturated aqueous solution of sodium hydrogen carbonate and saturated brine. After washing, anhydrous magnesium sulfate was added to the organic layer to dry it, and the resulting mixture was gravity-filtered to give a filtrate. This filtrate was concentrated to give an oily substance. The obtained oily substance was purified by silica column chromatography. As the developing solvent, a 10:1 hexane-ethyl acetate mixed solvent was used. The obtained fraction was concentrated to give 0.85 g of a white solid in 20% yield. A synthesis scheme (a-1) of Step 1 is shown below.

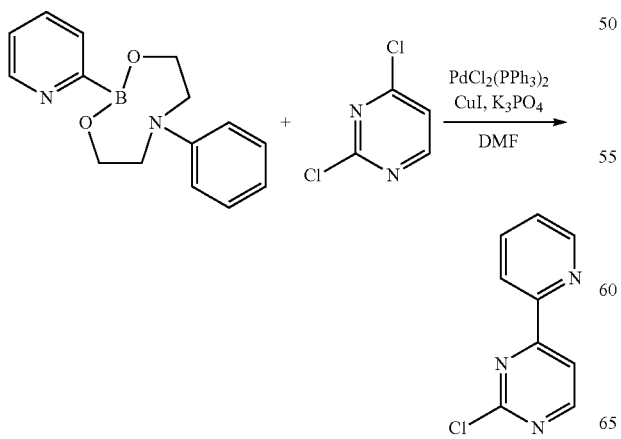

(a-1)

Step 2: Synthesis of 2,8-Bis(4,4,5,5-tetramethyl-1,3,2-dioxaboran-2-yl)dibenzofuran First, 3.0 g (7.1 mmol) of 2,8-diiododibenzofuran, 4.0 g (15.6 mmol) of bis(pinacolato)diboron, and 4.8 g (48.6 mmol) of potassium acetate were put into a flask, and the air in the flask was replaced with nitrogen. To this mixture, 70 mL of dehydrated dimethyl sulfoxide was added, and the mixture was degassed by being stirred under reduced pressure. To this mixture, 0.408 g (0.50 mmol) of bis(triphenylphosphine)palladium(II) dichloride was added, and the mixture was stirred under nitrogen stream at 90° C. for 19 hours. After that, dichloromethane was added to the obtained reaction mixture, and the solid was removed by suction filtration. The obtained filtrate was subjected to extraction. The solution obtained by the extraction and the organic layer were combined and washed with water three times. Anhydrous magnesium sulfate was added to this organic layer to dry it, and the resulting mixture was gravity-filtered to give a filtrate. This filtrate was concentrated to give an oily substance. The obtained oily substance was purified by silica column chromatography (neutral silica). As the developing solvent, a 10:1 hexane-ethyl acetate mixed solvent was used. The obtained fraction was concentrated to give 1.9 g of a white solid in 64% yield. A synthesis scheme (b-1) of Step 2 is shown below.

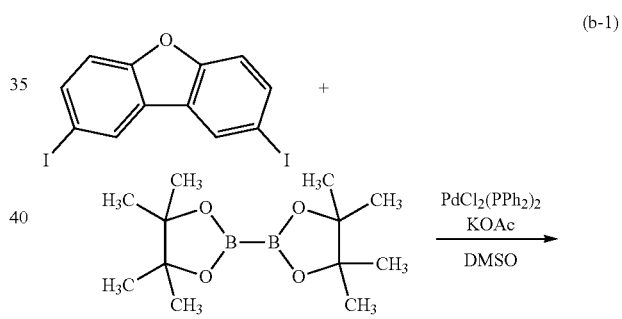

(b-1)

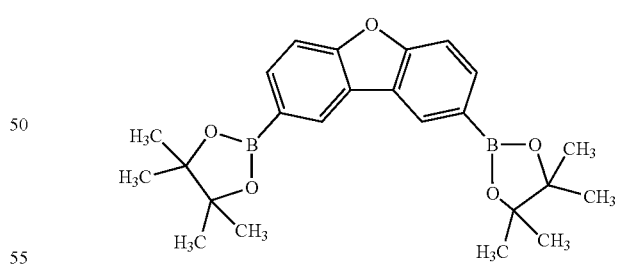

Step 3: Synthesis of PyPm2DBF-01

First, 0.88 g (2.1 mmol) of 2,8-bis(4,4,5,5-tetramethyl-1,3,2-dioxaboran-2-yl)dibenzofuran, which was synthesized in Step 2, 0.85 g (4.4 mmol) of 2-chloro-4-(2-pyridyl)pyrimidine, 22 ml of toluene, and 9 ml of ethanol were put into a 100-mL round-bottom flask, and the air in the flask was replaced with argon. Further, 0.194 g (0.168 mmol) of tetrakis(triphenylphosphine)palladium(0) was added to this mixture, and the mixture was bubbled with argon for 20 minutes. After a predetermined time had elapsed, 9 ml of a 2M aqueous solution of potassium carbonate was added. This reaction container was subjected to irradiation with microwaves (2.45 GHz, 150 W) for 1 hour to cause a reaction. After the reaction, the reaction mixture was cooled, and a solid was precipitated. Then, the reaction mixture was suction filtered, and the obtained solid was washed with water. Ethanol was added to the obtained solid, and the mixture was irradiated with ultrasonic waves and then suction filtered to give 0.72 g of a white solid in 72% yield. By a train sublimation method, 0.72 g of the obtained solid was purified. The purification was conducted by heating at 270° C. under a pressure of 2.1 Pa with a flow rate of argon gas of 5 mL/min for 22 hours. After the purification, 0.62 g of a solid of the desired product was obtained at a collection rate of 86%. Note that the irradiation with microwaves was performed using a microwave synthesis system (Discover, manufactured by CEM Corporation). A synthesis scheme (c-1) of Step 3 is shown below.

breviation: PyPm2DBF-02), which is an organic compound of one embodiment of the present invention, is described in detail.

Step 1: Synthesis of 4-Phenylpyridine-2-carboxamidine Hydrochloride

First, 9.2 g (51.3 mmol) of 4-phenylpyridine-2-carbonitrile and 100 mL of methanol (dehydrated) were put into a 300-mL three-neck flask. Then, 127 mg (2.36 mmol) of sodium methoxide was added to this mixture, and the mixture was stirred under a nitrogen stream at room temperature for 16 hours. After a predetermined time had elapsed, 2.7 g (51.3 mmol) of ammonium chloride was added to the mixture, and the mixture was stirred under a nitrogen stream at room temperature for 18 hours. After a reaction, the reaction mixture was concentrated, and ethyl acetate was added to the mixture. The mixture was irradiated with ultrasonic waves and then suction filtered to give 10.8 g of a white solid in 90% yield. A synthesis scheme (a1-2) of Step 1 is shown below.

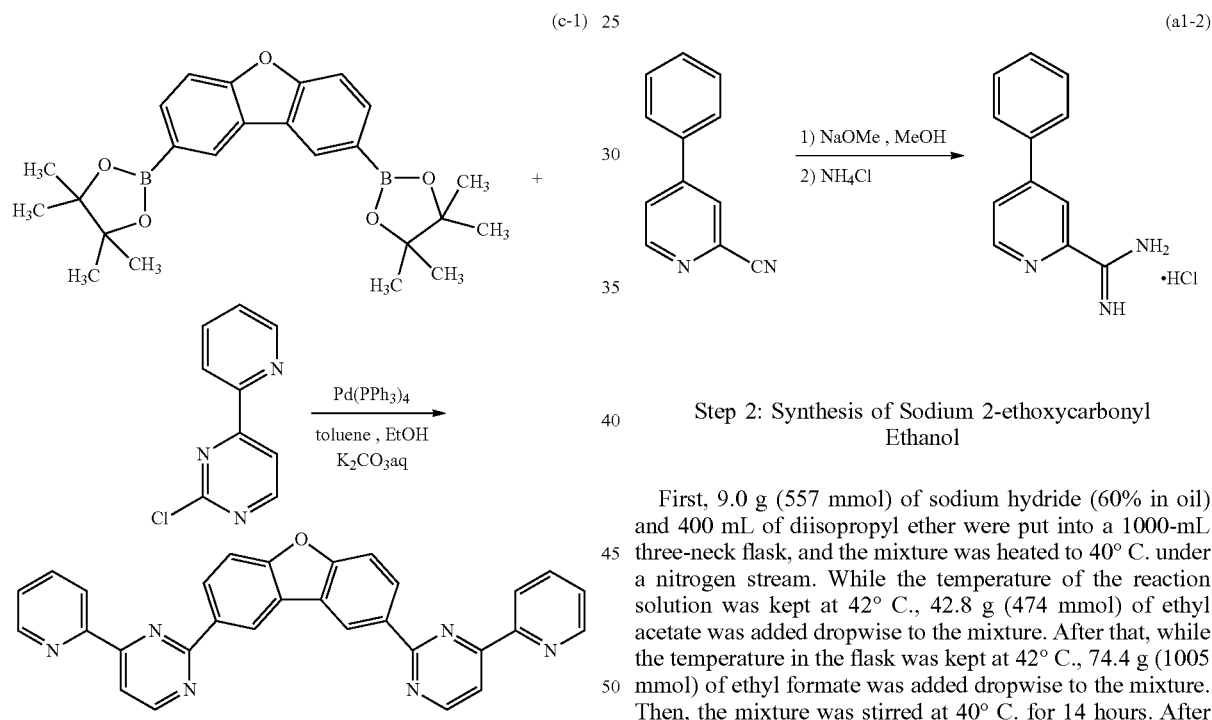

(c-1)

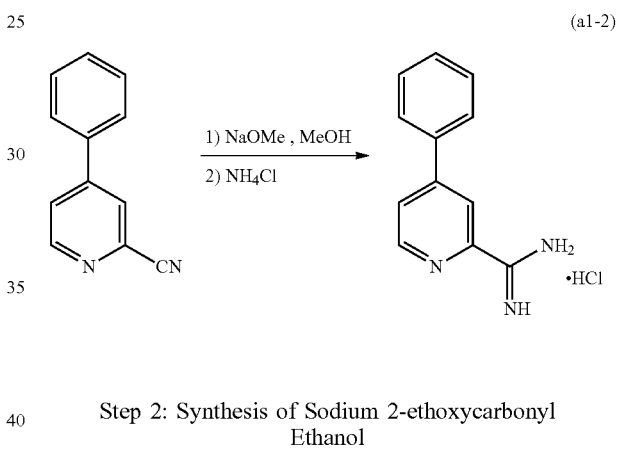

(a1-2)

The obtained substance was measured by $^1$H NMR. Measurement results are as follows. $^1$H-NMR. δ (DMSO-D$_6$): 7.66 (t, 2H), 7.93 (d, 2H), 8.16 (d, 2H), 8.32 (d, 2H), 8.80-8.83 (m, 4H), 8.92 (d, 2H), 9.12 (d, 2H), 9.53 (s, 2H)

Figure 13A:
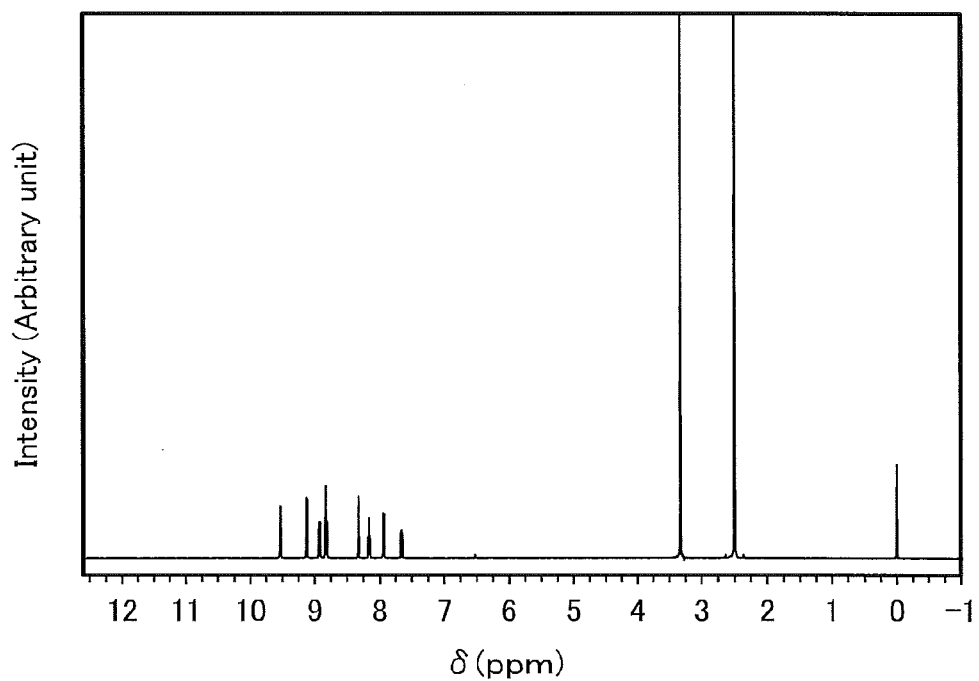
FIGS. 13A and 13B show $^1$H NMR charts of PyPmDBF-01.
Figure 13B:
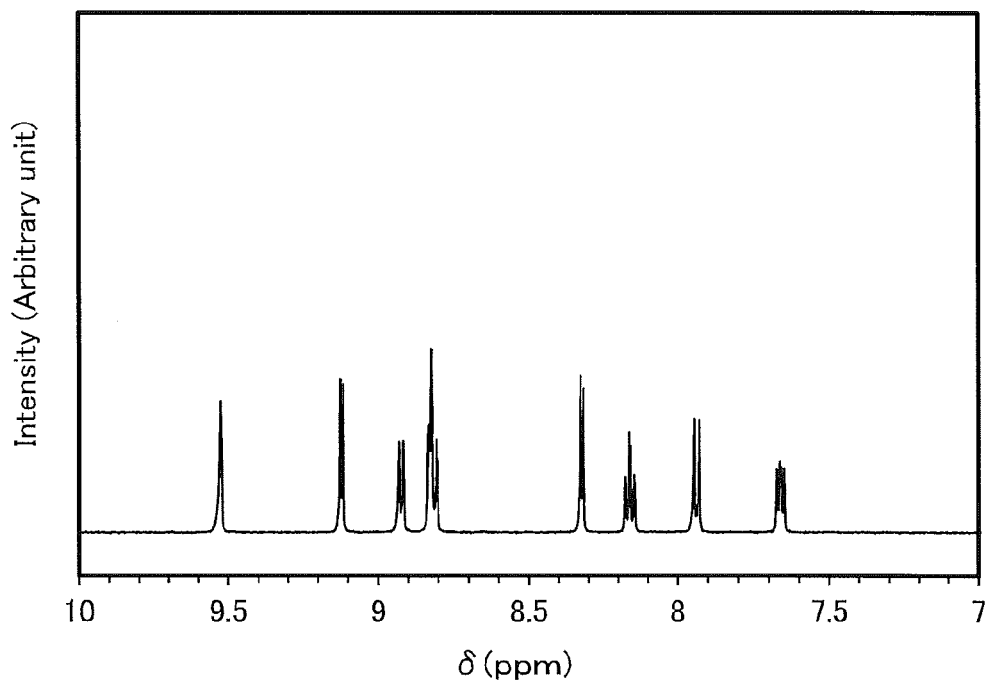

FIGS. 13A and 13B show $^1$H NMR charts. Note that FIG. 13B is a chart showing an enlarged part of FIG. 13A in the range of 7 ppm to 10 ppm. The charts reveal that PyPm2DBF-01 represented by the above structural formula (100), which is an organic compound of one embodiment of the present invention, was obtained.

Example 2

In this example, a method of synthesizing 4,4'-(dibenzofuran-2,8-diyl)bis[2-(4-phenylpyridin-2-yl)pyrimidine] (ab- Step 2: Synthesis of Sodium 2-ethoxycarbonyl Ethanol First, 9.0 g (557 mmol) of sodium hydride (60% in oil) and 400 mL of diisopropyl ether were put into a 1000-mL three-neck flask, and the mixture was heated to 40° C. under a nitrogen stream. While the temperature of the reaction solution was kept at 42° C., 42.8 g (474 mmol) of ethyl acetate was added dropwise to the mixture. After that, while the temperature in the flask was kept at 42° C., 74.4 g (1005 mmol) of ethyl formate was added dropwise to the mixture. Then, the mixture was stirred at 40° C. for 14 hours. After a reaction, the reaction mixture was suction filtered to give a solid. The obtained solid was washed with hexane to give 17.9 g of a white solid in 27% yield. A synthesis scheme (a2-2) of Step 2 is shown below.

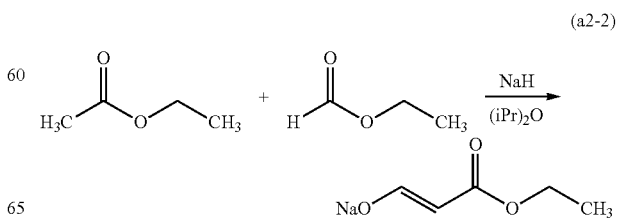

(a2-2)

Step 3: Synthesis of 2-(4-Phenylpyridin-2-yl)pyrimidin-4(3H)-one

First, 10.8 g (46.2 mmol) of 4-phenylpyridine-2-carboxamidine hydrochloride, 17.9 g (129.8 mmol) of sodium 2-ethoxycarbonyl ethanol, and 220 mL of ethanol (dehydrated) were put into a 1000-mL recovery flask. Then, 3.1 g (46.2 mmol) of sodium ethoxide was added to this mixture, and the mixture was heated under a nitrogen stream at 90° C. for 14 hours. This reaction mixture was concentrated to give a residue. Then, 80 ml of water and ethyl acetate were added to the obtained residue. The mixture was irradiated with ultrasonic waves and then suction filtered to give 7.7 g of a white solid in 67% yield. A synthesis scheme (a3-2) of Step 3 is shown below.

Step 4: Synthesis of 4-Chloro-2-(4-phenylpyridin-2-yl)pyrimidine

First, 7.7 g (30.8 mmol) of 2-(4-phenylpyridin-2-yl)pyrimidin-4(3H)-one and 60 mL of phosphoryl chloride were put into a 200-mL three-neck flask, and the mixture was heated under a nitrogen stream at 100° C. for 7 hours. Ice was slowly added to this mixture, and the mixture was stirred for 12 hours. Chloroform was added and dissolved in this mixture. The aqueous layer and the organic layer of this mixture were separated, and extraction of the aqueous layer was performed with chloroform. The solution obtained by the extraction and the organic layer were combined and washed with a saturated aqueous solution of sodium hydrogen carbonate and then saturated brine. After that, anhydrate magnesium sulfate was added to the organic layer to dry it, and the resulting mixture was gravity-filtered to give a filtrate. The obtained filtrate was condensed to give a solid. The obtained solid was recrystallized with toluene, so that 5.3 g of a white solid was obtained in 65% yield. A synthesis scheme (a4-2) of Step 4 is shown below.

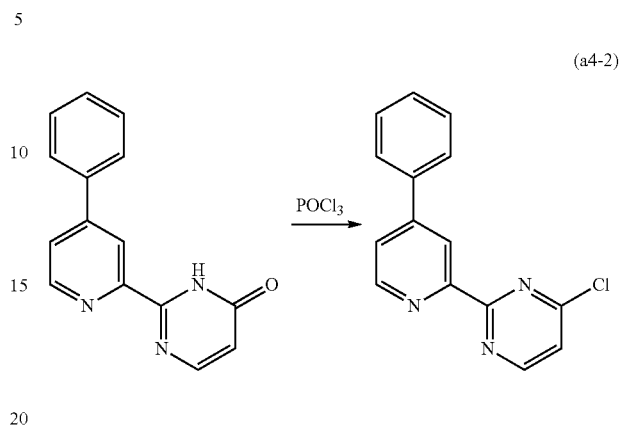

Step 5: Synthesis of 2,8-Bis(4,4,5,5-tetramethyl-1,3,2-dioxaboran-2-yl)dibenzofuran This step was similar to Step 2 in Example 1.

Step 6: Synthesis of PyPm2DBF-02

First, 2.4 g (5.6 mmol) of 2,8-bis(4,4,5,5-tetramethyl-1,3,2-dioxaboran-2-yl)dibenzofuran, 3.5 g (12.9 mmol) of 4-chloro-2-(4-phenylpyridin-2-yl)pyrimidine, 50 ml of toluene, 15 ml of ethanol, and 13 ml of a 2M aqueous solution of potassium carbonate were put into a 200-mL three-neck flask. The mixture was degassed by replacing the air in the flask with nitrogen under reduced pressure. Further, 0.518 g (0.448 mmol) of tetrakis(triphenylphosphine)palladium(0) was added to this mixture, and the mixture was stirred at 90° C. for 12 hours. After the reaction, the reaction mixture was cooled. And a solid was precipitated. Then, the reaction mixture was suction filtered, and the obtained solid was washed with water and ethanol. Furthermore, 300 mL of toluene was added to the obtained solid, and the mixture was heated and refluxed. This mixture was filtered, so that 0.92 g of a solid was obtained in 26% yield. A synthesis scheme (c-2) of Step 6 is shown below.

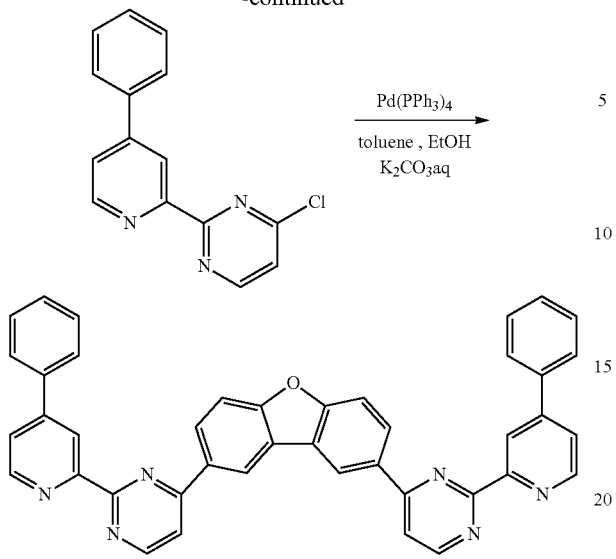

The obtained substance was measured by $^1$H NMR. Measurement results are as follows. $^1$H-NMR. δ (DMSO-D$_6$): 7.53 (t, 2H), 7.59 (t, 4H), 7.91-7.96 (m, 6H), 8.01 (d, 2H), 8.32 (d, 2H), 8.65 (d, 2H), 8.79 (s, 2H), 8.93 (d, 2H), 9.13 (d, 2H), 9.32 (s, 2H)

Figure 14A:
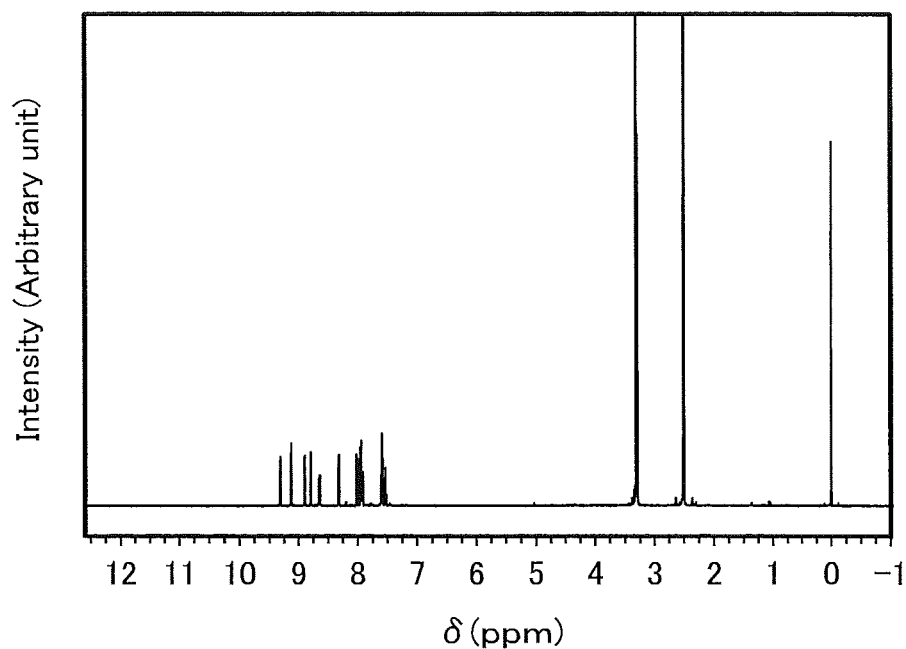
FIGS. 14A and 14B show $^1$H NMR charts of PyPmDBF-02.
Figure 14B:
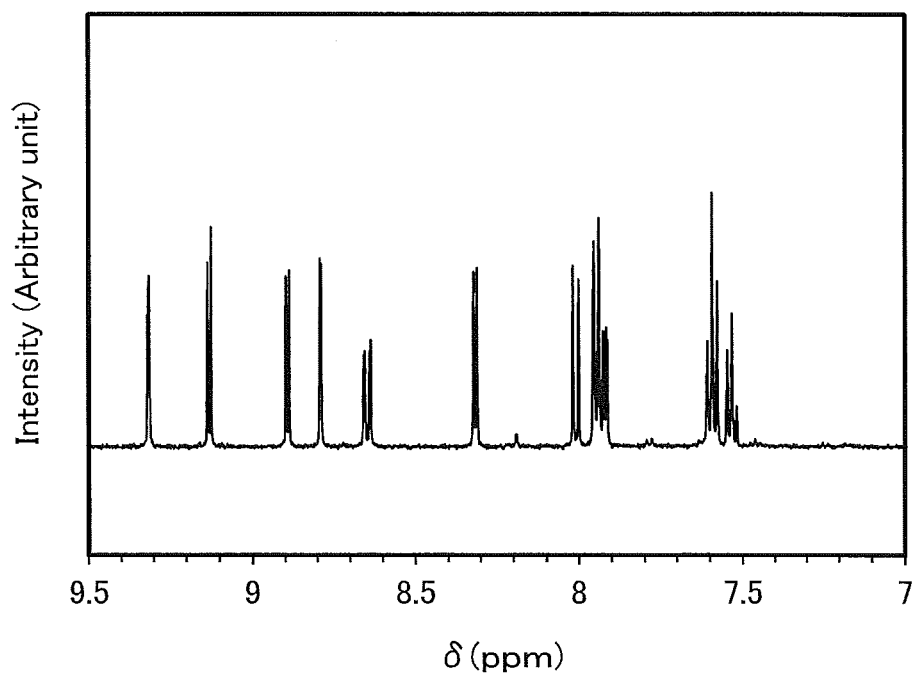

FIGS. 14A and 14B show $^1$H NMR charts. Note that FIG. 14B is a chart showing an enlarged part of FIG. 14A in the range of 7 ppm to 9.5 ppm. The charts reveal that PyPm2DBF-02 represented by the above structural formula (200), which is an organic compound of one embodiment of the present invention, was obtained.

Example 3

In this example, a method of synthesizing 5,5'-(dibenzofuran-2,8-diyl)diphenanthroline (abbreviation: 2,8Phen2DBf), which is an organic compound of one embodiment of the present invention, is described in detail.

Step 1: Synthesis of 2,8-Bis(4,4,5,5-tetramethyl-1,3,2-dioxaboran-2-yl)dibenzofuran This step was similar to Step 2 in Example 1.

Step 2: Synthesis of 2,8Phen2DBf

First, 2.3 g (5.5 mmol) of 2,8-bis(4,4,5,5-tetramethyl-1,3,2-dioxaboran-2-yl)dibenzofuran, 2.6 g (12.0 mmol) of 5-chloro-1,10-phenanthroline, 28 ml of dioxane, and 13 ml of a 2M aqueous solution of potassium phosphate were put into a 100-mL round-bottom flask. The mixture was bubbled with argon for 20 minutes. After a predetermined time had elapsed, 0.302 g (0.33 mmol) of tris(dibenzylidineacetone)palladium(0) and 1.3 ml (0.792 mmol) of a 20% toluene solution of tricyclohexylphosphine were added to the mixture. This reaction container was subjected to irradiation with microwaves (2.45 GHz, 150 W) for 2 hours to cause a reaction. After the reaction, the reaction mixture was cooled, and a solid was precipitated. Then, the reaction mixture was suction filtered, and the obtained solid was washed with water. Ethanol was added to the obtained solid, and the mixture was irradiated with ultrasonic waves and then suction filtered to give a white solid. Dichloromethane was added to the obtained solid to remove an insoluble portion by gravity filtration, and the obtained filtrate was concentrated to give a solid. Ethyl acetate was added to the obtained solid. The mixture was irradiated with ultrasonic waves and then suction filtered to give 1.5 g of a white solid in 54% yield. By a train sublimation method, 1.5 g of the obtained solid was purified (under a pressure of 3.4 Pa with a flow rate of argon gas of 5 mL/min at 350° C. for 16 hours). After the purification, 0.58 g of a solid of the desired product was obtained at a collection rate of 39%. Note that the irradiation with microwaves was performed using a microwave synthesis system (Discover, manufactured by CEM Corporation). A synthesis scheme (c-3) of Step 2 is shown below.

(c-3)

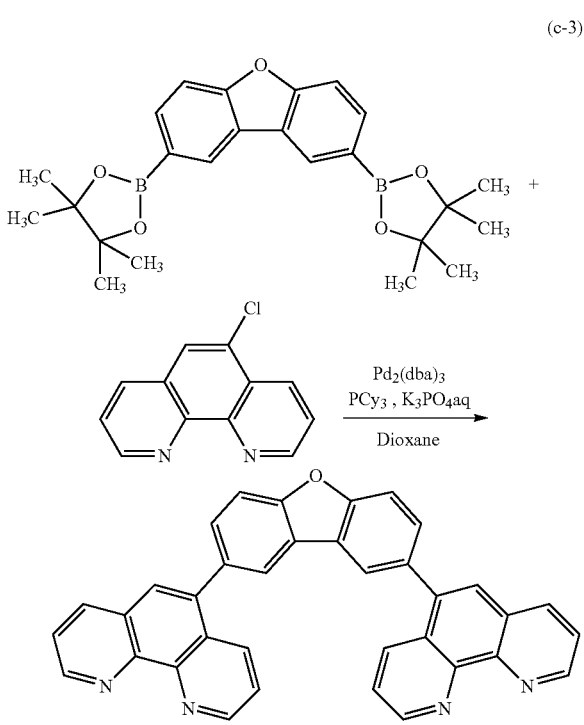

The obtained substance was measured by $^1$H NMR. Measurement results are as follows. $^1$H-NMR. δ (CDCl$_3$): 7.59-7.61 (m, 2H), 7.67-7.70 (m, 4H), 7.82-7.85 (m, 4H), 8.16 (s, 2H), 8.28 (dd, 2H), 8.33 (dd, 2H), 9.22-9.24 (m, 4H)

Figure 15A:
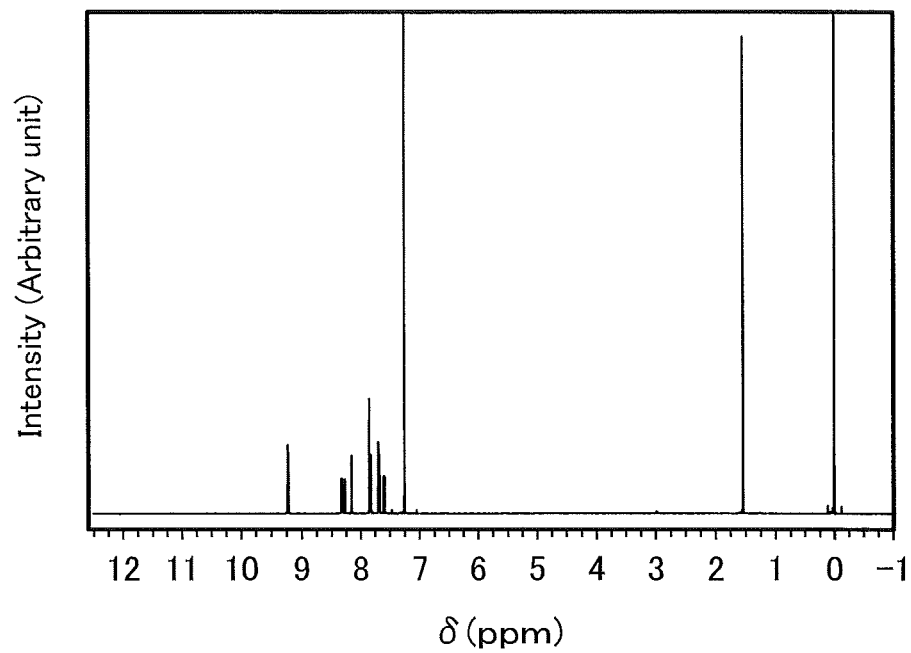
FIGS. 15A and 15B show $^1$H NMR charts of 2,8Phen2DBf-01.
Figure 15B:
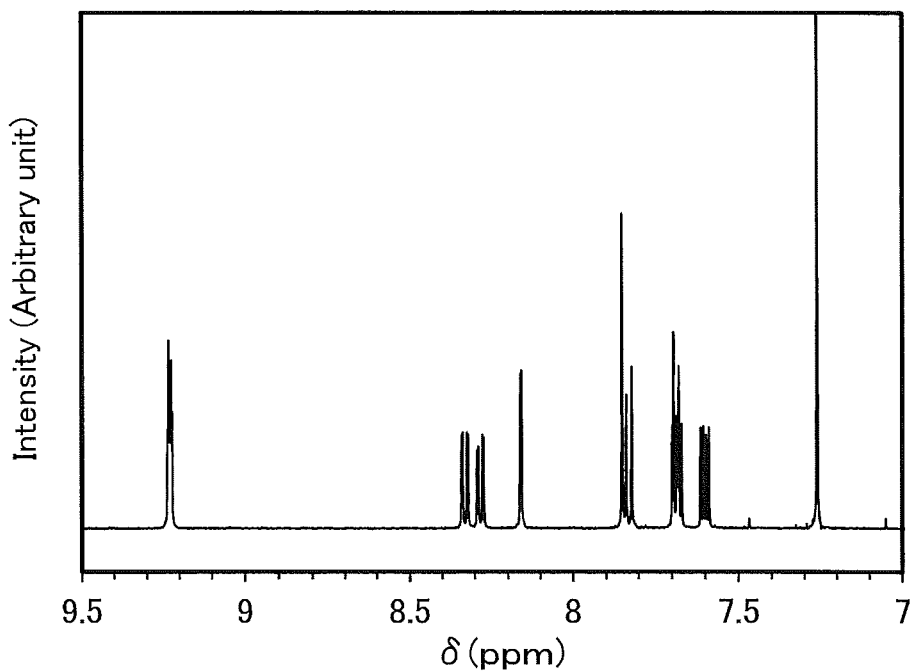

FIGS. 15A and 15B show $^1$H NMR charts. Note that FIG. 15B is a chart showing an enlarged part of FIG. 15A in the range of 7 ppm to 9.5 ppm. The charts reveal that 2,8Phen2DBf represented by the above structural formula (200), which is an organic compound of one embodiment of the present invention, was obtained.

Example 4

In this example, a method of synthesizing 2,2'-(dibenzofuran-2,8-diyl)diphenanthroline (abbreviation: 2,8Phen2DBf-02), which is an organic compound of one embodiment of the present invention, is described in detail.

Step 1: Synthesis of 2,8-Bis(4,4,5,5-tetramethyl-1,3,2-dioxaboran-2-yl)dibenzofuran This step was similar to Step 2 in Example 1.

Step 2: Synthesis of 2,8Phen2DBf-02

First, 2.0 g (4.8 mmol) of 2,8-bis(4,4,5,5-tetramethyl-1,3,2-dioxaboran-2-yl)dibenzofuran, 2.3 g (10.6 mmol) of 2-chloro-1,10-phenanthroline, 28 ml of dioxane, and 13 ml of a 2M aqueous solution of potassium phosphate were put into a 100-mL round-bottom flask. The mixture was bubbled with argon for 20 minutes. After a predetermined time had elapsed, 0.266 g (0.29 mmol) of tris(dibenzylidineacetone)palladium(0) and 1.0 ml (0.696 mmol) of a 20% toluene solution of tricyclohexylphosphine were added to the mixture. This reaction container was subjected to irradiation with microwaves (2.45 GHz, 150 W) for 2 hours to cause a reaction. After the reaction, dichloromethane was added to the reaction mixture, and the mixture was separated into an aqueous layer and an organic layer. Extraction of the aqueous layer was performed. The solution obtained by the extraction and the organic layer were combined and washed with water, a saturated aqueous solution of sodium hydrogen carbonate, and a saturated aqueous solution of sodium chloride. Anhydrous magnesium sulfate was added to this organic layer to dry it, and the resulting mixture was filtered through a filter aid in which Celite (produced by Wako Pure Chemical Industries, Ltd., Catalog No. 531-16855, the same applies in this example), alumina, and Celite were stacked in this order. Furthermore, the mixture was washed with 2 L of ethyl acetate, and the obtained filtrate was concentrated to give a solid. Ethyl acetate was added to the obtained solid, and the mixture was irradiated with ultrasonic waves and then suction filtered to give 0.75 g of a white solid of the desired product in 30% yield. Note that the irradiation with microwaves was performed using a microwave synthesis system (Discover, manufactured by CEM Corporation). A synthesis scheme (c-4) of Step 2 is shown below.

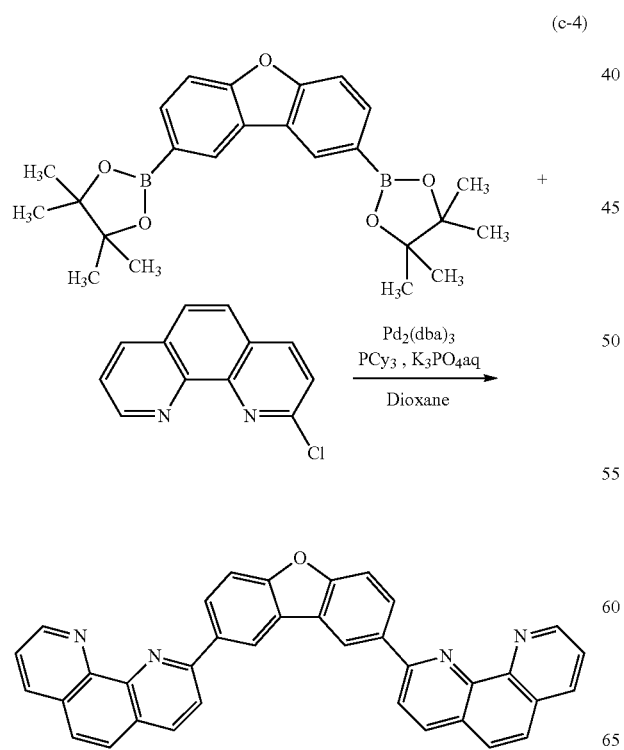

(c-4)

The obtained substance was measured by $^1$H NMR. Measurement results are as follows. $^1$H-NMR. δ (CDCl$_3$): 7.66-7.69 (m, 2H), 7.77-7.88 (m, 6H), 8.26-8.30 (m, 4H), 8.40 (d, 2H), 8.56 (dd, 2H), 9.10 (s, 2H), 9.29 (dd, 2H)

Figure 16A:
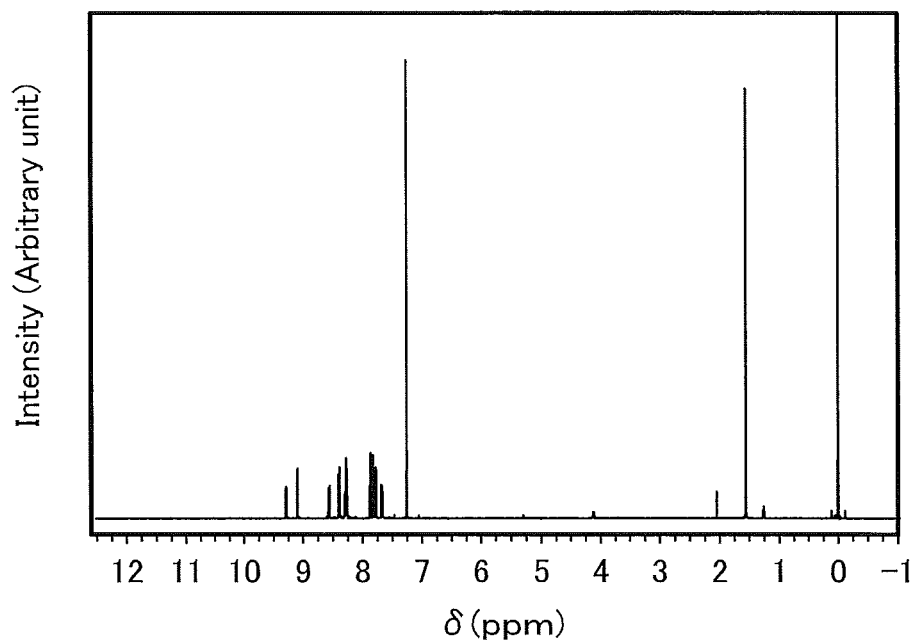
FIGS. 16A and 16B show $^1$H NMR charts of 2,8Phen2DBf-02.
Figure 16B:
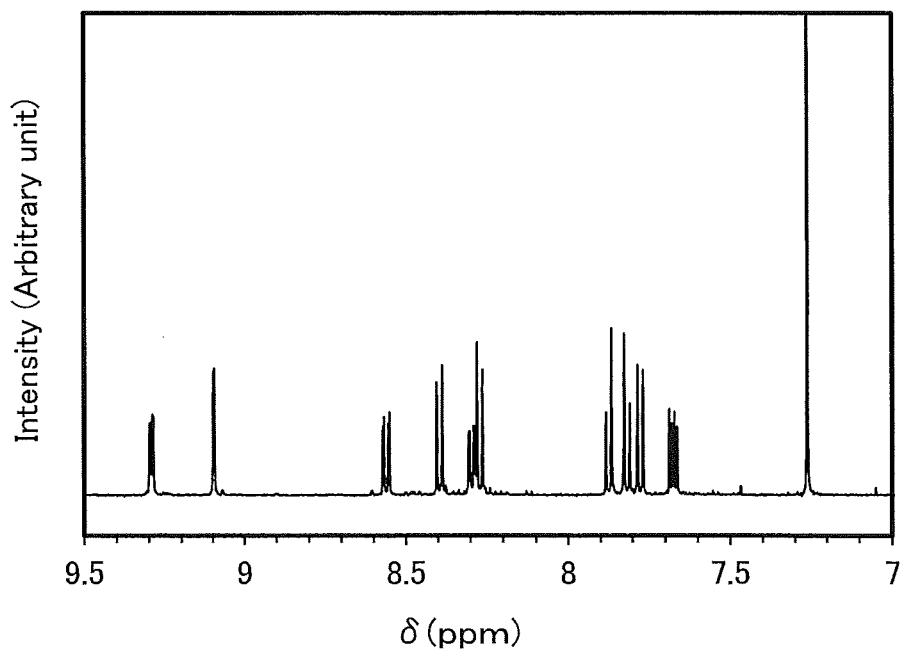

FIGS. 16A and 16B show $^1$H NMR charts. Note that FIG. 16B is a chart showing an enlarged part of FIG. 16A in the range of 7 ppm to 9.5 ppm. The charts reveal that 2,8Phen2DBf-02 represented by the above structural formula (200), which is an organic compound of one embodiment of the present invention, was obtained.

Example 5

In this example, a light-emitting element (light-emitting element 1) of one embodiment of the present invention is described. Structural formulae of organic compounds used in the light-emitting element 1 are shown below.

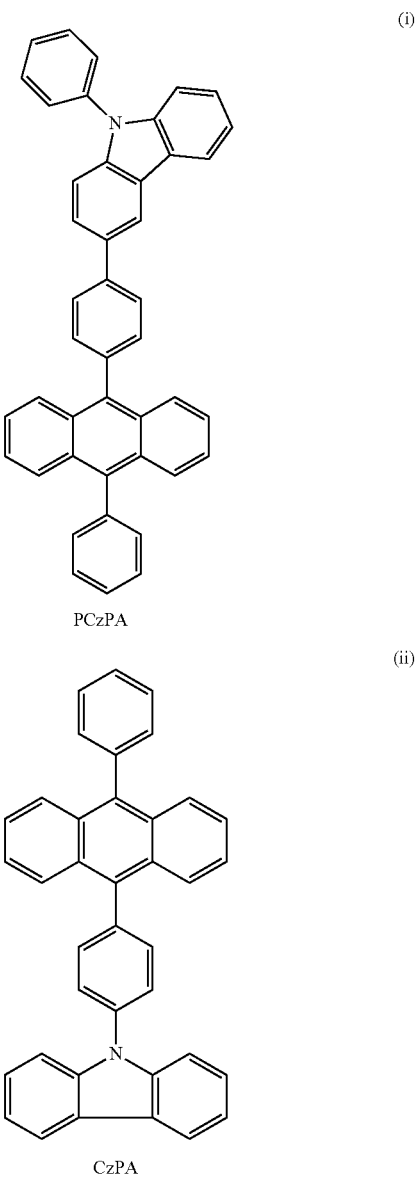

(i) PCzPA (ii) CzPA

-continued (iii)

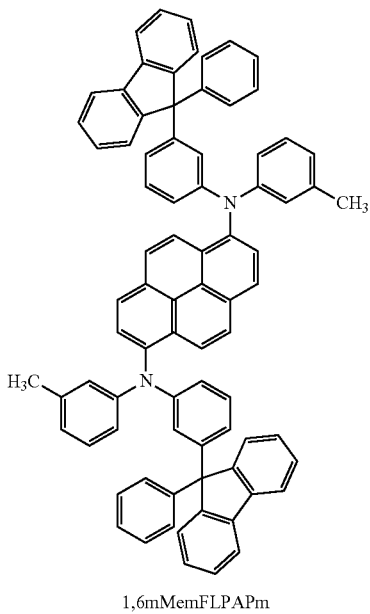

1,6mMemFLPAPrn (iv)

(v)

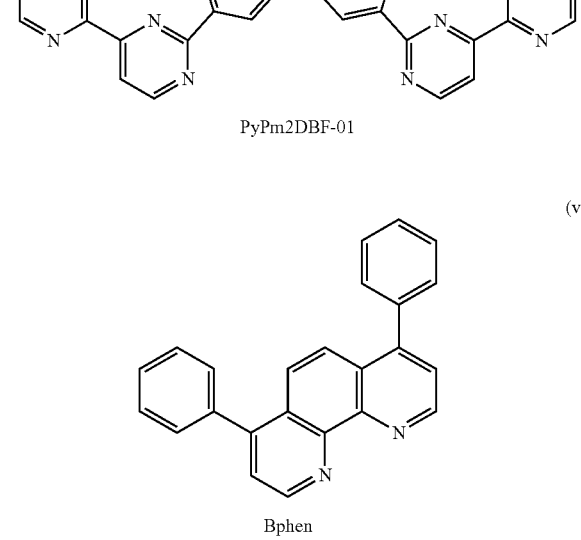

Bphen

A method of manufacturing the light-emitting element 1 of this example is described below.

(Manufacturing Method of Light-Emitting Element 1)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 is an electrode that functions as an anode of the light-emitting element.

Next, as pretreatment for forming the light-emitting element over the substrate, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate over which the first electrode 101 was formed was fixed to a substrate holder provided in the vacuum evaporation apparatus so that the surface on which the first electrode 101 was formed faced downward. The pressure in the vacuum evaporation apparatus was reduced to about $10^{-4}$ Pa. After that, over the first electrode 101, 9-phenyl-3-[4-(10-phenyl-9-anthryl)phenyl]-9H-carabzole (abbreviation: PCzPA) represented by the above structural formula (i) and molybdenum(VI) oxide were deposited by co-evaporation by an evaporation method using resistance heating, so that the hole-injection layer 111 was formed. The thickness of the hole-injection layer 111 was set to 50 nm, and the weight ratio of PCzPA to molybdenum oxide was adjusted to 4:2 (=PCzPA:molybdenum oxide). Note that the co-evaporation method refers to an evaporation method in which evaporation is carried out from a plurality of evaporation sources at the same time in one treatment chamber.

Next, a film of PCzPA was formed to a thickness of 10 nm over the hole-injection layer 111, so that the hole-transport layer 112 was formed.

Furthermore, over the hole-transport layer 112, the light-emitting layer 113 was formed by co-evaporation of 9-[4-(10-phenyl-9-anthryl)phenyl]-9H-carbazole (abbreviation: CzPA) represented by the above structural formula (ii) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (iii) with a weight ratio of 1:0.04 (=CzPA:1,6mMemFLPAPrn) to a thickness of 25 nm.

Then, the electron-transport layer 114 was formed over the light-emitting layer 113 in such a manner that a 10 nm thick film of 2,2'-(dibenzofuran-2,8-diyl)bis[4-(2-pyridyl)pyrimidine] (abbreviation: PyPm2DBF-01) represented by the above structural formula (iv) was formed and a 15 nm thick film of bathophenanthroline (abbreviation: BPhen) represented by the above structural formula (v) was further formed.

After the formation of the electron-transport layer 114, lithium fluoride (LiF) was deposited by evaporation to a thickness of 1 nm to form the electron-injection layer 115. Lastly, a 200 nm thick film of aluminum was deposited by evaporation to form the second electrode 102 functioning as a cathode. Thus, the light-emitting element 1 was fabricated.

The light-emitting element 1 was sealed using a glass substrate in a glove box containing a nitrogen atmosphere so as not to be exposed to the air (specifically, a sealing material was applied onto an outer edge of the element and UV treatment and heat treatment at 80° C. for 1 hour were performed at the time of sealing). Then, reliability of the light-emitting element was measured. Note that the measurements were carried out at room temperature (in an atmosphere kept at 25° C.).-

Figure 17:
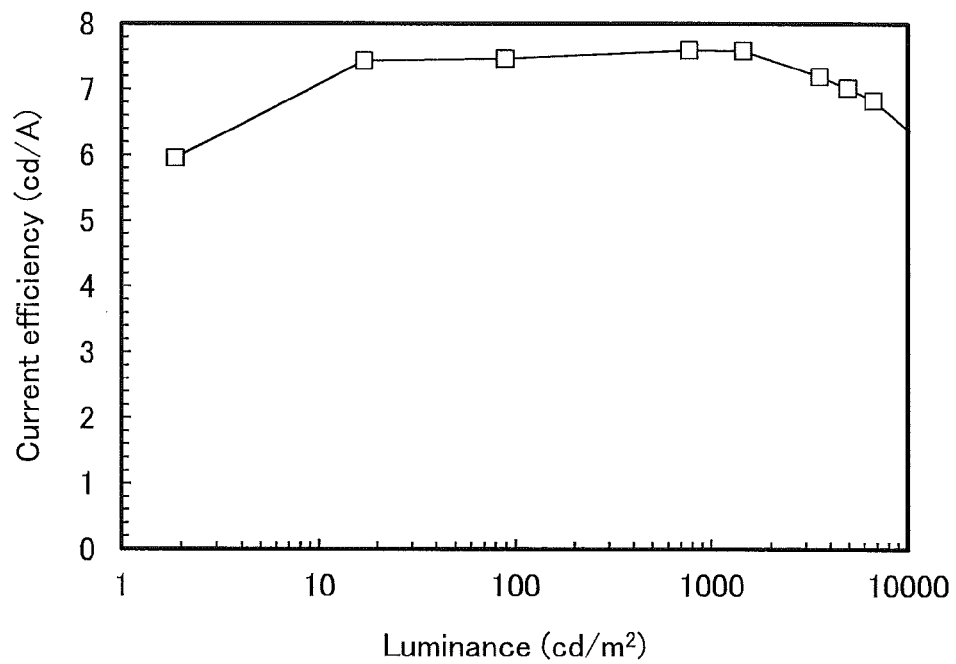
FIG. 17 shows luminance-current efficiency characteristics of a light-emitting element 1.
Figure 18:
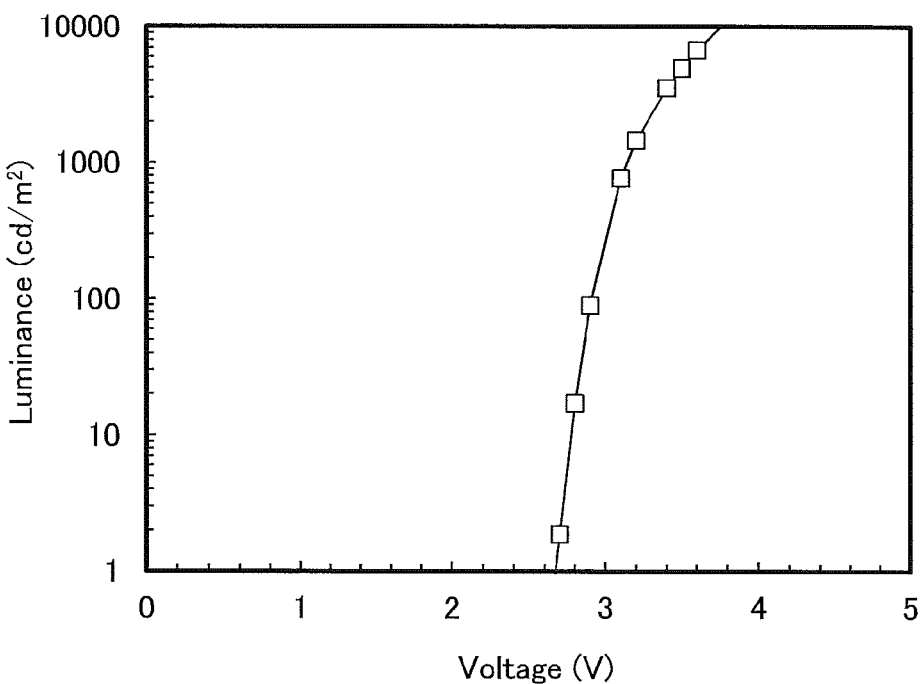
FIG. 18 shows voltage-luminance characteristics of the light-emitting element 1.
Figure 19:
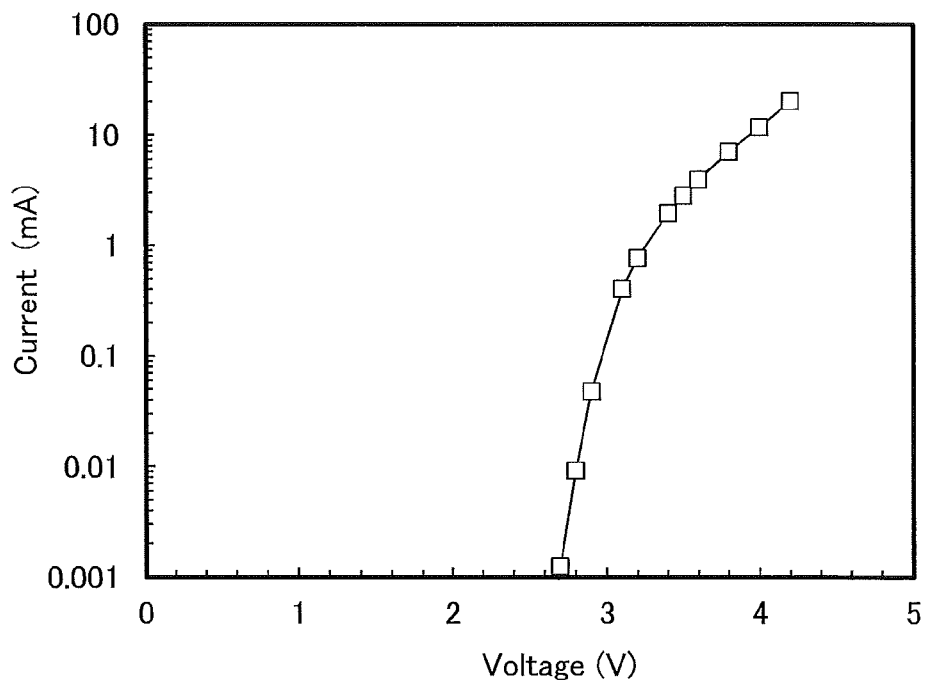
FIG. 19 shows voltage-current characteristics of the light-emitting element 1.
Figure 20:
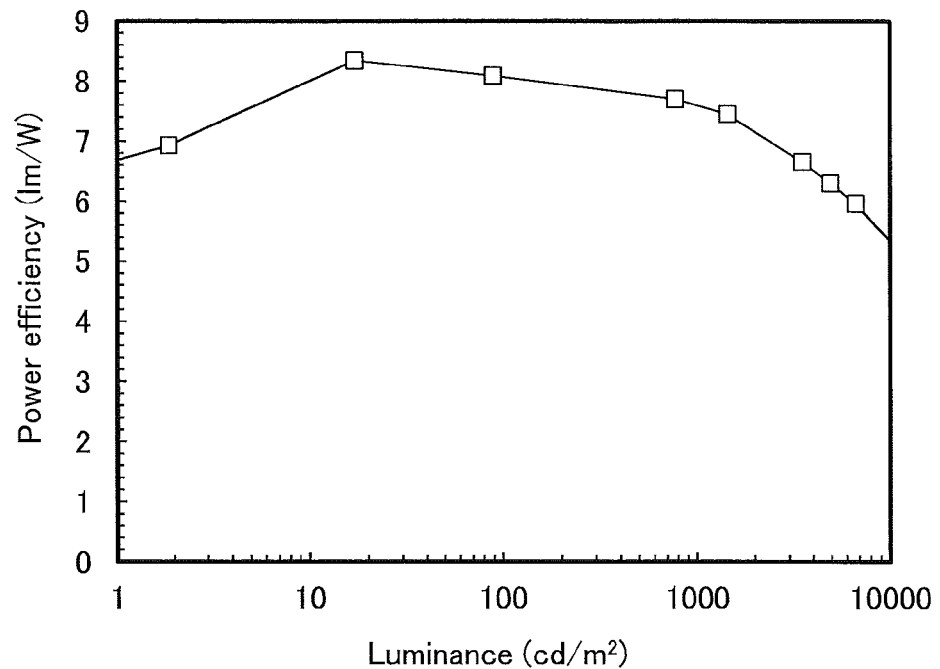
FIG. 20 shows luminance-power efficiency characteristics of the light-emitting element 1.
Figure 21:
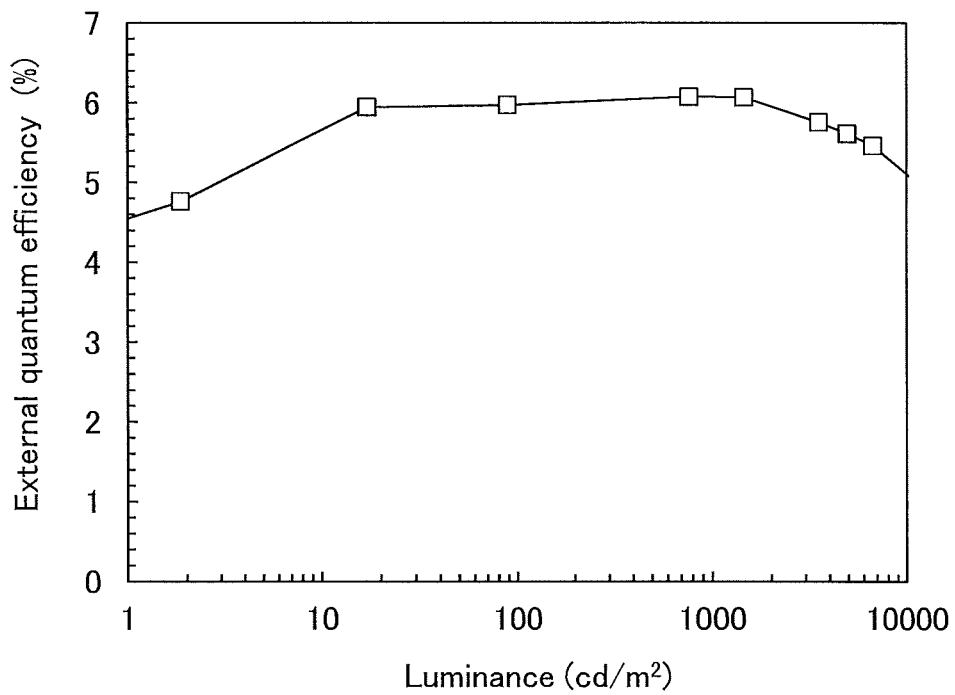
FIG. 21 shows luminance-external quantum efficiency characteristics of the light-emitting element 1.
Figure 22:
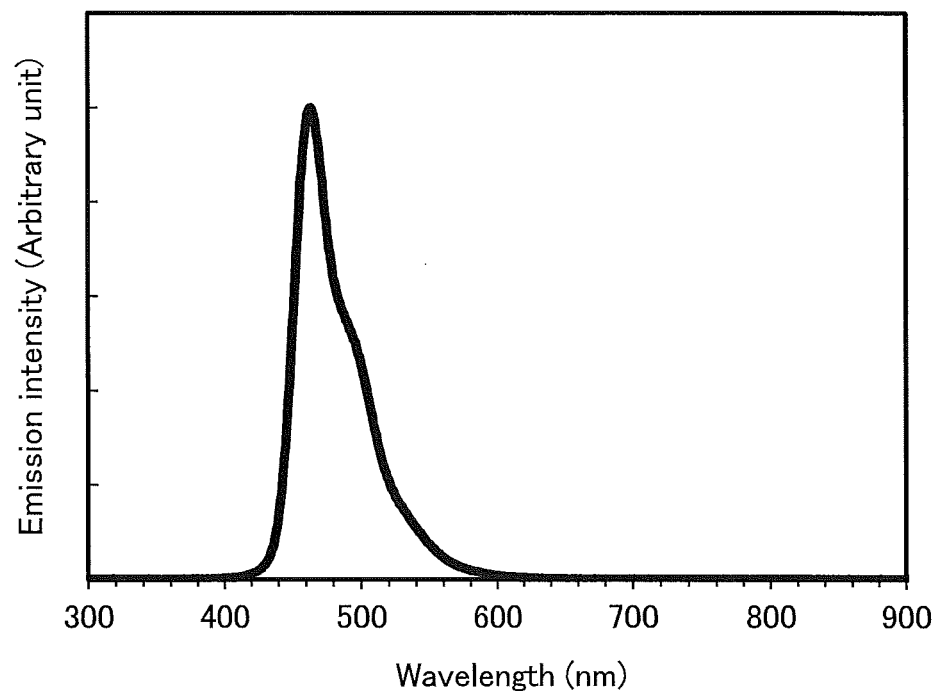
FIG. 22 shows an emission spectrum of the light-emitting element 1.

FIG. 17 shows luminance-current efficiency characteristics of the light-emitting element 1; FIG. 18 shows voltage-luminance characteristics thereof; FIG. 19 shows voltage-current characteristics thereof; FIG. 20 shows luminance-power efficiency characteristics thereof; FIG. 21 shows luminance-external quantum efficiency characteristics thereof; and FIG. 22 shows an emission spectrum thereof.

The results show that the light-emitting element 1 has excellent characteristics. The results also show that the light-emitting element 1 has low drive voltage because of the excellent carrier-transport property of PyPm2DBF-01 and thus has excellent power efficiency.

As described above, it is found that the light-emitting element 1 including PyPm2DBF-01, which is one embodiment of the present invention, is a successful light-emitting element that has excellent characteristics (particularly, low drive voltage and high power efficiency).

This application is based on Japanese Patent Application serial no. 2013-234790 filed with the Japan Patent Office on Nov. 13, 2013, the entire contents of which are hereby incorporated by reference.

What is claimed is:

1. A compound represented by a general formula (G2),

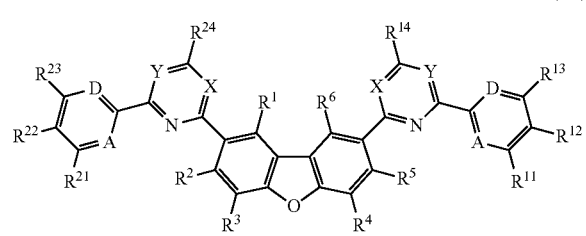

(G2)

wherein $R^1$ to $R^6$, $R^{11}$ to $R^{14}$, and $R^{21}$ to $R^{24}$ separately represent any one of a hydrogen, an alkyl group having 1 to 6 carbon atoms, and a substituted or unsubstituted phenyl group, wherein X and Y separately represent a carbon atom or a nitrogen atom, and wherein A and D separately represent a carbon atom or a nitrogen atom, and at least one of A and D represents a nitrogen atom.

2. The compound according to claim 1,
wherein A represents a carbon atom,
wherein D represents a nitrogen atom, and
wherein X represents a nitrogen atom.

3. The compound according to claim 1,
wherein A represents a carbon atom,
wherein D represents a nitrogen atom, and
wherein Y represents a nitrogen atom.

4. The compound according to claim 1, wherein the compound is represented by a structural formula (100),

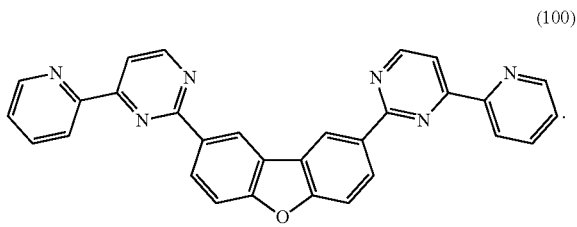 [SMILES: c1ccc(-c2ccnc(-c3ccc4oc5ccc(-c6nccc(-c7ccccn7)n6)cc5c4c3)n2)nc1]

(100)

5. The compound according to claim 1, wherein the compound is represented by a structural formula (200),

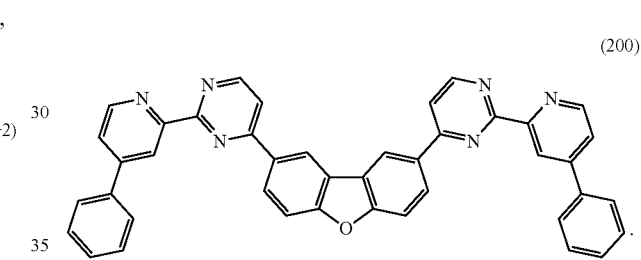

(200)

6. A light-emitting device comprising:
a light-emitting element comprising the compound according to claim 1; and
a unit capable of controlling the light-emitting element.

7. A display device comprising:
a display portion comprising a light-emitting element comprising the compound according to claim 1; and
a unit capable of controlling the light-emitting element.

8. A lighting device comprising:
a lighting portion comprising a light-emitting element comprising the compound according to claim 1; and
a unit capable of controlling the light-emitting element.

9. An electronic device comprising a light-emitting element comprising the compound according to claim 1.

10. A compound represented by a general formula (G3),

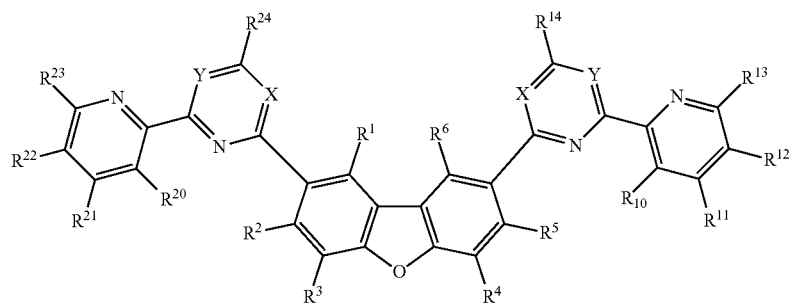

(G3)

wherein $R^1$ to $R^6$ separately represent any one of a hydrogen, an alkyl group having 1 to 6 carbon atoms, and a substituted or unsubstituted phenyl group, wherein $R^{10}$ to $R^{14}$ and $R^{20}$ to $R^{24}$ separately represent an alkyl group having 1 to 6 carbon atoms or a substituted or unsubstituted phenyl group, and wherein one of X and Y represents a carbon atom and the other of X and Y represents a nitrogen atom.

11. The compound according to claim 10, wherein X represents a nitrogen atom.

12. The compound according to claim 10, wherein Y represents a nitrogen atom.

13. A light-emitting device comprising:
a light-emitting element comprising the compound according to claim 10; and
a unit capable of controlling the light-emitting element.

14. A display device comprising:
a display portion comprising a light-emitting element comprising the compound according to claim 10; and
a unit capable of controlling the light-emitting element.

15. A lighting device comprising:
a lighting portion comprising a light-emitting element comprising the compound according to claim 10; and
a unit capable of controlling the light-emitting element.

16. An electronic device comprising a light-emitting element comprising the compound according to claim 10.

\* \* \* \* \*